Figure 1:
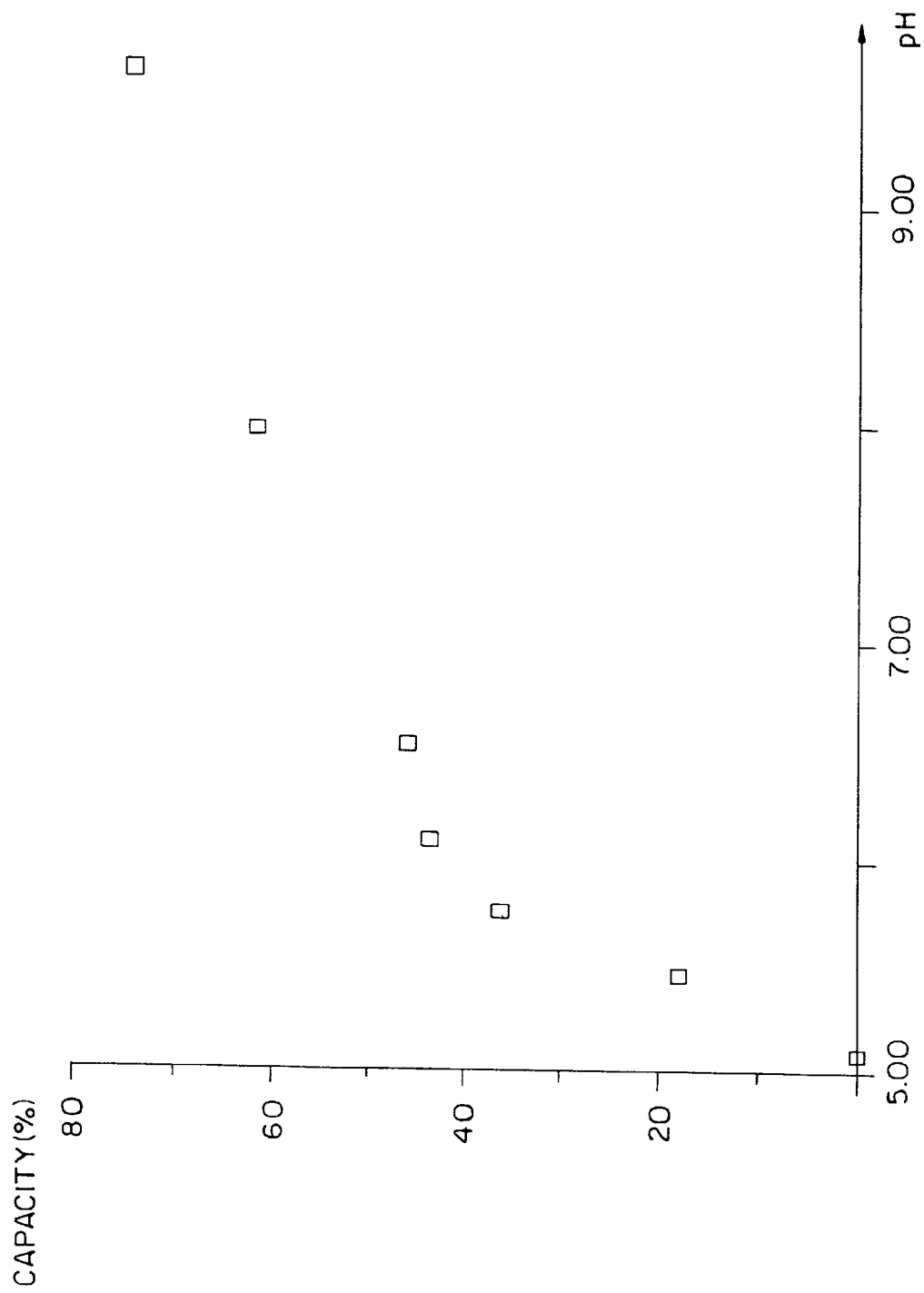

United States Patent [19]
Boisselier-Cocolios et al.

[11] Patent Number: 6,139,603
[45] Date of Patent: Oct. 31, 2000

[54] PROCESS FOR RECOVERING OXYGEN

[75] Inventors: Brigitte Boisselier-Cocolios, Limours; Roger Guilard, Fontaine-les-Dijon; Christophe Jean, Chenove; Laurent Taurin, Longjumeau, all of France

[73] Assignee: L'Air Liquide, Societe Anonyme pour l'Etude et l'Exploitation des Procedes Georges Claude, Paris Cedex, France

[21] Appl. No.: 08/253,233

[22] Filed: Jun. 2, 1994

Related U.S. Application Data

[62] Continuation of application No. 08/253,233, Jun. 2, 1994, which is a continuation of application No. 07/582,911, filed as application No. PCT/FR90/00124, Feb. 22, 1990, abandoned.

[30] Foreign Application Priority Data

Feb. 22, 1989 [FR] France .................................. 89 02315

[51] Int. Cl.⁷ ....................... C07C 229/16; C07D 257/02
[52] U.S. Cl. ..................................... 95/44; 95/54; 95/138; 95/178; 95/230; 252/1; 540/465; 540/467; 540/474
[58] Field of Search ..................................... 540/465, 467, 540/474; 95/44, 54, 138, 178, 230; 252/1

[56] References Cited

U.S. PATENT DOCUMENTS

| | | | |
|---|---|---|---|
| 2,751,390 | 6/1956 | Bersworth | 546/264 |
| 2,781,389 | 2/1957 | Mannheimer | 558/25 |
| 4,678,667 | 7/1987 | Meares et al. | 540/465 |
| 4,702,998 | 10/1987 | Tanaka et al. | 540/474 |
| 4,789,745 | 12/1988 | Lin | 546/301 |
| 4,885,363 | 12/1989 | Tweedle et al. | 540/465 |

FOREIGN PATENT DOCUMENTS

| | | |
|---|---|---|
| 23559/84 | 7/1988 | Australia . |
| 37058/89 | 1/1990 | Australia . |
| 76217/87 | 12/1990 | Australia . |
| 11685/88 | 1/1991 | Australia . |
| 199880/88 | 11/1991 | Australia . |
| 0099685 | 2/1984 | European Pat. Off. . |
| 1287436 | 10/1988 | European Pat. Off. . |
| 0292689 | 11/1988 | European Pat. Off. . |
| 0768849 | 2/1972 | Germany . |
| 87/06229 | 10/1987 | WIPO . |
| 89/01476 | 2/1989 | WIPO . |
| 8901475 | 2/1989 | WIPO .................................... 540/474 |
| 89/11475 | 11/1989 | WIPO . |

OTHER PUBLICATIONS

Journal of the Chemical Society, No. 6, Mar. 1984, C. Raleigh et al.: "Autoxidation pathways of $Co^{II}$–complexes of pyridyl–containing pentamines involving dioxygen compleses as intermediates", pp. 335–336.

Inorganic Chemistry, vol. 14, No. 10, Oct. 1975, G. McLendon et al.: "Combination of dioxygen with N,N–bis (2–aminoethyl) glycinatocobalt (II) and with diethylenetriamine–N–acetatocobalt (II)", pp. 2322–2326.

Martin Studer et al., Helv. Chim. Acta. vol. 69, pp. 2081–2086, 1986.

Gries et al, "Chemical Abstract", 109(1), 1988 #6552X.

*Primary Examiner*—John M. Ford
*Assistant Examiner*—Pavanaram K Sripada
*Attorney, Agent, or Firm*—Browdy and Neimark

[57] ABSTRACT

Method for recovering oxygen from a medium containing $O_2$ using polynitrogenated compounds that have five coordinating functions which are capable of binding a metal atom, particularly a cobalt atom. In the recovery method, oxygen is first absorbed by the metal complex and then desorbed from the complex and recovered in an appropriate vessel.

10 Claims, 4 Drawing Sheets

PROCESS FOR RECOVERING OXYGEN

This application is a continuation of application Ser. No. 08/253,233, filed Jun. 2, 1994, which is a continuation of application Ser. No. 07/582,911, filed Oct. 12, 1990 now abandoned which is a 371 of PCT/FR90/00124, filed Feb. 22, 1990.

This invention relates to polynitrogenated compounds, the metal complexes of which are $O_2$ carriers. It relates also to the preparation of these compounds and of their metal complexes as well as to their use for the separation of dioxygen from a gas mixture. In the following, "oxygen" will mean the molecular oxygen or dioxygen ($O_2$). Since the discovery by Calvin et al. in 1946 of Cobalt Schiff base molecules capable of reversibly binding dioxygen, numerous other complexes have been proposed for the separation of dioxygen from a gas mixture and its selective recovery by desorption.

The complex that is contacted with the gaseous mixture containing dioxygen can be in the solid state or in solution in aqueous or organic media.

The most currently used complexes in aqueous solutions are the linear or cyclic polyamines, the polyamine ethers or the aminoacids, these molecules beeing coordinated to a metal such as cobalt. The above-mentioned compounds possess at least three nitrogenated groups as coordination sites, that is to say, groups that are able to participate to a coordination bond with a metal. Nitrogenated groups represent any group that possess at least one nitrogen atom such as primary, secondary or tertiary amine groups, or heterocycle groups. The particular interest of a complex relates to different physico-chemical characteristics, especially its dioxygen affinity at a given concentration and its lifetime.

The separation of $O_2$ from a gas mixture comprises two main steps. the first one being the absorption of dioxygen by an appropriate complex, the second one being the desorption of dioxygen.

It is then obvious that the affinity constant of a complex must not be too high for the desorption energy to be reasonably low. Among the most common desorption modes, one can distinguish the vacuum desorption method and the electrochemical desorption method.

In the case of vacuum desorption as described in the U.S. Pat. No. 4,393,711 (1982), the authors of the present invention determined that an ideal desorption condition, would be at a total pressure greater or equal to 0.07 bar at a temperature of 15° C. At a concentration of 0.1 M, the affinity constant of the complex should be in the range $10^4$ to $10^7$ $M^{-1}$ L for the vacuum desorption to be effective.

In the case of an electrochemical desorption, as described in the European patent # 0 283 761 of 1988, the complex must be electroactive or must be capable of being oxidized or reduced by an electron transfer from an electrode, and must have a dioxygen affinity constant equal or greater than $10^7$ $M^{-1}$ L. Moreover, the longer the lifetime of the complex the higher its commercial interest.

The longest lifetime observed today for an $O_2$ carrier in aqueous medium is of the order of one month at a concentration of $10^{-3}$ M as reported by Mc. Lendon et al., Inorganic Chemistry, Vol 14, N°10, 2322–2326, 1975, for the cobalt complex of the following ligand:

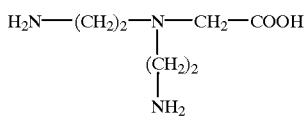

At the concentration of $10^{-1}$ M, this complex degrades faster, its lifetime being reduced to about five days.

This invention is based on the demonstration made by the inventors that some functionalized groups in a determined compound induce a decrease of the dioxygen binding constant of the resulting cobalt complex and an increase of its lifetime.

This invention relates to polynitrogenated compounds that possess specific functions and that are capable of dioxygen binding after complexation of a metal.

This invention also provides dioxygen carriers that can be used in aqueous solutions and present a lifetime greater than one year at the concentration of $10^{-1}$ M.

This invention also provides a method of preparation of these polynitrogenated compounds and of their metal complexes for industrial use.

Moreover this invention provides a process for the separation of dioxygen from a gas mixture by absorption and its recovery by desorption under low energy consumption conditions.

The polynitrogenated compounds of the invention are represented by the following general formula I:

where y is equal to 0 or 1.
a) if y=0
$x_1$ and $x_2$ are equal to 0 or 1, and $x_1$ and $x_2$ are not simultaneously equal to 0;
A, B and C, identical or different, represent:
an alkyl chain —$(CH_2)_x$— in which x represents an integer ranging from 1 to 4, this alkyl chain being substituted or not by one or several groups P or by one or several groups $P_1$, where $P_1$ represents an alkyl group of 1 to 4 carbon atoms eventually substituted by one or several groups P, where P represents:
a —COR group where R represents a hydroxyl (—OH), a primary ammine or an amine substituted by one or two alkyl groups of 1 to 4 carbon atoms, a —OR' function where R' represents an alkyl group of 1 to 4 carbon atoms or an aromatic cycle of 6 to 14 carbon atoms, or an aromatic cycle of 6 to 14 carbon atoms eventually substituted in its ortho and/or meta and/or para position by a halide, an alkyl group of 1 to 4 carbon atoms, an alkoxy of 1 to 4 carbon atoms, a hydroxy, an aryl group, an aromatic heterocycle, a nitro group, a group —$(CH_2)_t$COR where R has the above mentioned meaning and t is an integer ranging from 0 to 4, or a primary amine or an amine substituted by one or two alkyl groups of 1 to 4 carbon atoms.
an aromatic cycle of 6 to 14 carbon atoms eventually substituted in its ortho and/or meta and/or para positions by a halogen atom, an alkyl group of 1 to 4 carbon atoms, an alcoxy group of 1 to 4 carbon atoms, a hydroxy, an aryl group, an aromatic heterocycle, a nitro group, a —(CH$_2$)$_t$—COR group in which R has the same meaning as above and t is an integer number ranging from 0 to 4, or a primary amine or an amine substituted by one or two alkyl groups or 1 to 4 carbon atoms.

an aromatic heterocycle, especially a nitrogenated heterocycle, of 4 to 12 carbon atoms, eventually substituted in its ortho, and/or meta, and/or para positions by an halogen atom, an alkyl group of 1 to 4 carbon atoms, an alcoxy group of 1 to 4 carbon atoms, a hydroxy, an aromatic heterocycle, an aryl group, a nitro group, a —(CH$_2$)$_t$—COR in which R has the same meaning as above and t represents an integer number ranging from 0 to 4, or a primary amine or an amine substituted by one or two alkyl groups of 1 to 4 carbon atoms.

a primary amine or an amine substituted by one or two alkyl groups of 1 to 4 carbon atoms.

a —CN group an alkyl group of 1 to 4 carbon atoms an alcoxy group of 1 to 4 carbon atoms a hydroxy group a nitro group an halogen atom an aromatic cycle of 6 to 14 carbon atoms in which 2 carbon atoms respectively participate to a bond with W and X when A is in the chain, or with X and Y when B is in the chain, or with Y and Z when C is in the chain. This aromatic cycle may be substituted by one or several groups P and or P$_1$, P and P$_1$ having the same meaning as described above.

a group represented by —(CH$_2$)$_{x3}$—V—(CH$_2$)$_{x4}$ in which x$_3$ and x$_4$ are integers varying from 1 to 3 and V represents an aromatic cycle of 6 to 14 carbon atoms, that can be substituted by one or several groups P and or P$_1$, P and P$_1$ having the same meaning as above.

X and Y, identical or different, respectively represent:

if x$_1$ and X$_2$ are both equal to 1:

a group

in which P$_2$ represents a hydrogen atom or a group P or a group P$_1$, P and P$_1$ having the same meaning as above.

an aromatic heterocycle containing a nitrogen atom and 4 to 12 carbon atoms, two of which participating to bonds with A and B when X is in the chain or with B and C when Y is in the chain, this heterocycle being substituted or not by one or several groups P and/or P$_1$, P and P$_1$ having the same meaning as above.

if x$_1$=0 or if x$_2$=0: Y or X are respectively terminal groups and represent:

a —COR group in which R has the same meaning as above an aromatic heterocycle that contains a nitrogen atom and 4 to 12 carbon atoms substituted or not in its ortho and/or meta and/or para positions by one or several groups P and/or P$_1$, P and P$_1$, having the same meaning as above.

a CN group.

a

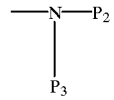

group where P$_2$ and P$_3$, identical or different, represent a hydrogen atom or the groups P or P$_1$, P and P$_1$ having the same meaning as above, W and Z, identical or different represent respectively the groups indicated above for X and Y when x$_1$ or x$_2$ are respectively equal to zero, or also an aromatic cycle of 6 to 14 carbon atoms, substituted or not by one or several groups P and/or P$_1$, P and P$_1$ having the same meaning as above, being excluded the compounds of formula

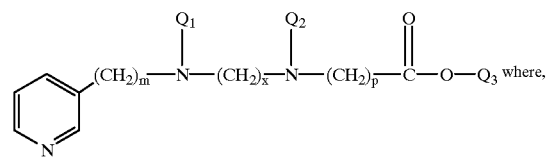 where, m and p are integers ranging from 1 to 4, n is an integer ranging from 2 to 4, Q$_1$ and Q$_2$, identical or different are a hydrogen atom or an alkyl group of 1 to 4 carbon atoms, Q$_3$ is a hydrogen atom, an alkyl group of 1 to 4 carbon atoms or a phenyl group substituted or not by one, two or three substituants chosen among the followings: a chlorine atom or an alkyl group of 1 to 3 carbon atoms.

b) if y=1, x$_1$ and x$_2$ equal 1

D has the same meaning than A, B, and C as described above

W, X, Y and Z, identical or different, represent respectively:

the groups listed above for X and Y when x$_1$ and x$_2$ are respectively equal to 1, or an aromatic cycle of 6 to 14 carbon atoms in which two carbon atoms participate respectively to a bond with A and D when W is in the chain, or with B and A when X is in the chain, or with C and B when Y is in the chain, or with D and C when Z is in the chain, this aromatic cycle being eventually substituted by one or several groups P and/or P$_1$, P and P$_1$ having the same meaning as above, or a group represented by —(CH$_2$)$_{x3}$—V—(CH$_2$)$_{x4}$— in which x$_3$ and x$_4$ are integers varying from 1 to 3 and V represents an aromatic cycle of 6 to 14 carbon atoms, eventually substituted by one or several groups P and/or P$_1$, P and P$_1$ having the same meaning as above, a group

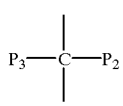

in which P$_2$ and P$_3$ have the same meaning as above, whereas it is understood that, y being equal to 0 or 1, the polynitrogenated compounds possess 4 or 5 coordination sites, one of them being a COR group where R has the same meaning as above, while the other sites are groups that contain a nitrogen atom such as:
the groups

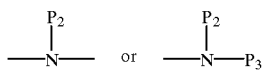

in which $P_2$ and $P_3$ have the same meaning than above, the aromatic nitrogenated heterocycles that contain 4 to 12 carbon atoms, and that are eventually substituted by one or several groups P and/or $P_1$ as defined above, whereas, when the polynitrogenated compounds possess 4 coordination sites, then either the three nitrogenated groups are

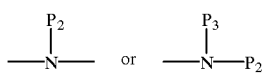

groups as defined above and then the polynitrogenated compounds possess an aromatic cycle of 6 to 14 carbon atoms, eventually substituted by one or several groups P and/or $P_1$ as defined above, or one out of the three nitrogenated groups represents an aromatic heterocycle, eventually substituted by one or several groups P and/or $P_1$ as defined above, the compounds of formula α:

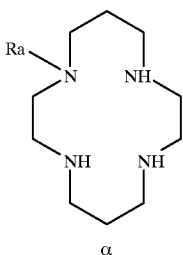

in which Ra represents:
a —(CH$_2$)$_n$—COOH group where n is an integer varying from 1 to 3,
or a

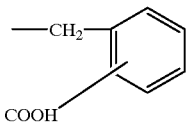

being excluded.

The aromatic heterocycles that are the nitrogenated groups mentionned above, are particularly chosen among the following groups: pyridine, imidazole, quinoline, isoquinoline, pyrrole, pyrimidine, pyrazine, pyridazine, indole, carbazole, purine, phenazine, thiazole, isothiazole, oxazole, isoxazole.

Among the aromatic cycles defined above are particularly considered the following groups : benzene, biphenyl, naphthalene, azulene, anthracene, phenanthracene.

This invention relates also to the salts of these compounds with mineral or organic acids, especially halides as chlorides, bromides, iodides or fluorides, or sulfates, phosphates, nitrates, or acetates and citrates.

The polynitrogenated compounds of this invention or their salts with mineral or organic acids may be found also as hydrates.

Due to the presence of the coordination group —COR, especially —COOH, and of 3 or 4 other nitrogenated functions, the compounds of this invention are remarquable reactants for the formation of stable metal complexes with a transition metal.

Preferred compounds of this invention are those corresponding to the following formula:

$$(W-A)_{x1}\text{-}X\text{-}B\text{-}Y\text{-}(C\text{-}Z)_{x2} \qquad (Ia)$$

in which W, A, X, B, Y, C, Z, $x_1$ and $x_2$ have the meanings indicated above when y=0.

Among the above-mentioned compounds Ia are particularly considered those corresponding to the formula Ib where $x_1=x_2=1$.

W-A-X-B-Y-C-Z

Other compounds of formula Ia may have $x_1$ or $x_2$ equal to zero.

The compounds that correspond to $x_1=0$ have the formula Ic:

X-B-Y-C-Z.

When $X_2=0$, they have the formula Id: W-A-X-B-Y.

Particularly advantageous are the compounds of formulae Ib, Ic and Id that possess 4 coordination groups.

Among the compounds of formula Ib, in which $x_1=x_2=1$, are especially considered those in which one of the W and Z groups represents the COR group, where R has the same meaning as above, while the other of the two, as well as X and Y, represent respectively a nitrogenated group.

The above mentioned compounds are especially advantageous when:

one of W or Z represents:
either a pyridyl, an imidazolyl or a pyrimidyl group
or an aminobenzyl group
X and Y represent respectively a —NH— group
A, B and C represent respectively a —(CH$_2$)$_x$ group, where x is an integer varying from 1 to 4.

Among the compounds of formula Ic, are especially considered those in which:

one of X or Z represents the —COR group, R having the same meaning as above, while the other of the two, as well as Y, represent a nitrogenated group and, one of B or C or Y, is substituted by an alkyl group of 1 to 4 carbon atoms substituted by a nitrogenated group.

The compounds of formula Ic are especially advantageous when:

one of X or Z represents
either a pyridyl, an imidazolyl or a pyrimidyl group,
or an aminobenzyl group,
or a primary amine —NH$_2$,
Y represents a

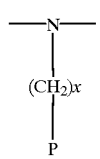

group where x is an integer varying from 1 to 4 and P represents:

either a pyridyl, an imidazolyl or a pyrimidyl group
or an aminobenzyl group
or a primary amine —NH$_2$,
   B and C respectively represent a —(CH$_2$)$_x$ group, x having the same definition as above.
   Among the compounds of formula Id, are especially considered those in which:
   one of W or Y represents a —COR group as defined above while the other of the two, as well as X, represent a nitrogenated group and,
   one of A or B or X, is substituted by an alkyl group of 1 to 4 carbon atoms, substituted by a nitrogenated group.
   Preferred compounds of formula Id are especially advantageous when:
   one of W or Y represents
either a pyridyl, a pyrimidyl or an imidazolyl group
or an aminobenzyl group
or a primary amine group —NH$_2$,
   X represents a

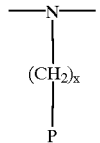

group, in which x is an integer varying from 1 to 4 and P represents:
either a pyridyl, an imidazolyl or a pyrimidyl group
or an aminobenzyl group
or a primary amine group —NH$_2$,
   A and B respectively represent a —(CH$_2$)$_x$ group, where x is as defined above.
   One of the advantageous aspects of this invention, relates to the above mentioned compounds of formula Ia that possess 5 coordination sites.
   Among these, preferred compounds correspond to formula Ib in which:
   W, X, Y and Z represent a nitrogenated group,
   one of W or Z is substituted by an alkyl group of 1 to 4 carbon atoms substituted by a —COR group where R has the above meaning.
   The above mentioned compounds are advantageously characterized by:
   one of W or Z represents
either a pyridyl, an imidazolyl or a pyrimidyl group,
or an aminobenzyl group
or a primary amine group —NH$_2$,
   while the other of the two, represents a —NH—(CH$_2$)$_x$—COR group in which R and x have the same meanings as above,
   X and Y respectively represent a —NH— group.
   A, B, C respectively represent a —(CH$_2$)$_x$ group, where x has the same meaning as above.
   Among the compounds of formula Ib that possess five coordination sites, are especially considered those charaterized by:
   one of W or Z represents a —COR group, R having the same meaning as above
   while the other of the two, as well as X and Y represent a nitrogenated group and,
   one of A, X, B, Y or C is substituted by an alkyl group of 1 to 4 carbon atoms, substituted by a nitrogenated group.

The above mentioned compounds are especially advantageous when:
   one of W or Z represents:
either a pyridyl, a pyrimidyl or an imidazolyl group
or an aminobenzyl group
or a primary amine groups —NH$_2$,
   one of X or Y represents a —NH— group while the other of the two represents

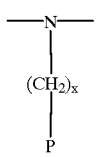

where x is an integer varying between 1 and 4 and P represents:
either a pyridyl, a pyrimidyl or an imidazolyl group
or an aminobenzyl group
or a primary amine group —NH$_2$
   A, B, C respectively represent —(CH$_2$)$_x$, x being as defined above.
   An other category of preferred compounds in this invention is represented by the compounds of the following general formula IIa:

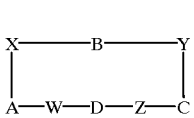

(IIa)

in which W, A, X, B, Y, C, Z and D have the same meanings as indicated above when y=1.
   Particularly advantageous are the compounds of formula IIa that possess 5 coordination sites and that are defined as:
   w, X, Y, and Z respectively represent a nitrogenated group,
   one of W, X, Y and Z is substituted by an alkyl group of 1 to 4 carbon atoms, this alkyl group being substituted by a —COR group where R has the same meaning as above.
   The above mentioned compound are especially advantageous when:
   W, X, Y and Z respectively represent:
   either a pyridyl, pyrimidyl or imidazolyl group eventually substituted by an alkyl group of 1 to 4 carbon atoms, this alkyl group being substituted by a —COR group, R having the same meaning as above.
   or a —NH— group or a

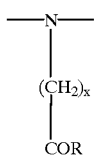

group where x and R have the same meaning as above.
   More generally, all the preferred compounds of this invention, as described above, possess advantageously a carboxylate group —COOH as the —COR group.

Among the compounds of formula Ia described in this invention are particularly advantageous the ones that possess an aromatic cycle, especially a phenyl group, and a COR group, especially a carboxylate group, respectively being terminal groups of the main chain of these compounds, i.e. the chain constituted by W and/or X, Y and/or Z.

Among such compounds are particularly considered the ones described as when $x_1=x_2$ (formula Ib), W or Z represents a phenyl group or an aminobenzyl group;

when $x_1=0$ (formula Ic) or when $x_2=$(formula Id), X or Z in the first case or, W or Y, in the second case, represent a phenyl group or an aminobenzyl group.

The preferred aspect of these compounds relates to the presence of the aromatic cycle added to the effect of the other coordination functions, that induces a good stability to the metal complexes formed with these ligands.

As an example of such ligand one can cite the following compound:

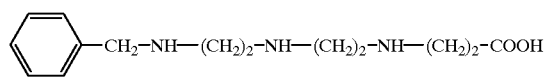

Particularly advantageous compounds of formula IIa are those in which W, X, Y and Z represent a secondary or a tertiary amine, one of these 4 constituants being substituted by a —(CH$_2$)$_x$—COR group, x and R being as defined above, while one other of these 4 constituents is substituted by an alkyl group of 1 to 4 carbon atoms, substituted itself by an aromatic cycle, especially a phenyl group.

The preferred aspect of these compounds is due to the same reasons as the ones mentioned above for compounds of formula Ia that possess a —COR group and an aromatic cycle.

It is also important to note that this cyclam like structure of formula II as precised above, is particularly advantageous for the formation of metal complexes; such a structure is indeed preformed in such a manner that coordination sites are preoriented and ready for metal complexation.

The advantageous aspect of the presence of an aromatic cycle in the structure of the above mentioned compounds, relates to its hydrophobicity and thus its capacity to restrict water molecules from going to the metal vicinity and from being activated.

As an example, a cyclam derivative particularly preferred is represented by the following formula:

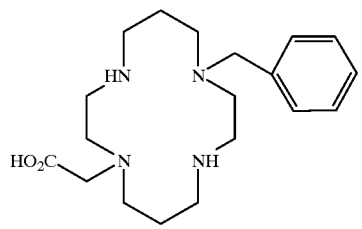

The preparation of the compounds described in this invention is essentially made by multistep reactions that involve classical organic chemistry pathways.

Thus the following reactions a), b) and c) are advantageously used for the synthesis of the compounds of this invention and more specifically for compounds of formula Ia.

a) In this first condensation, a reactant 1, especially an halide $R_1$-Z, is opposed to a primary amine 2, NH$_2$R$_2$, or a secondary amine 3,

according to the following scheme:

$R_1$—Z+H$_2$NR$_2$ or

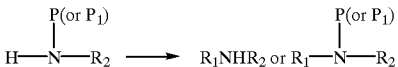

In the $R_1$-Z structure, Z is preferably a chlorine or a bromine atom.

$R_1$ corresponds to a part of the target final compound and is chosen among the groups that correspond to W—A—, (W—A)$_{x1}$—X—B, (W—A)$_{x1}$—X—B—Y—C, or —A—X—B—Y—C—Z, —B—Y—(C—Z)$_{x2}$ or —C—Z.

The compounds 2 and 3 mentioned above are then respectively chosen among the groups in which —NH—R$_2$ or

correspond to the following groups: —X—B—Y—(C—Z)$_{x2}$, —Y—(C—Z)$_{x2}$, —Z or W—, (W—A)$_{x1}$—X—, (W—A)$_{x1}$—X—B—Y, in which W, A, X, Y, B, C, Z, P, P$_1$, x$_1$ and x$_2$ have the meanings indicated above when y=0.

This reaction is advantageously realised in basic medium. Equimolar amounts of reactants are heated at temperatures preferably in the range 80 to 120° C.

b) In another condensation, an aldehyde 4 of formula R$_1$CHO where R$_1$ has the same meaning as in a), is reacted with a primary amine 2 as indicated in a), to yield a Schiff base, that is reduced in a second step reaction.

The scheme of this reaction is as follows:

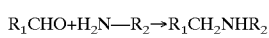

In the condensations a) and b) above-mentioned, the —COR function may be protected by appropriate groups as esters, this functions being revealed after reaction, by hydrolysis.

An other mean of introduction of the —COR coordination function in the intermediate compounds used in condensations a) and b) or in the final compounds obtained by using condensations a) and b) starting with reactants that do not possess —COR group, is effected by condensation, hereafter designed as condensation α, of an ester or acid halide Z—(CH$_2$)$_x$—COO(H, R') where x, Z and R' are as defined previously, and of an amine compound, intermediate or final, with or without protection on some of the amine functions, according to the following scheme:

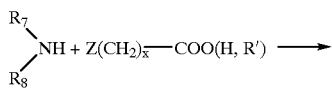

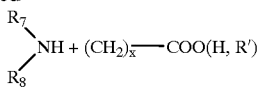

where $R_7$ and $R_8$ represent respectively a hydrogen atom or one of the groups indicated previously for $R_1$.

When the intermediate reactants used in the above mentioned condensations a) and b), do not possess a —COR function, it is especially advantageous to realize these condensations with a primary amine 2 $H_2N$—$R'_2$ (for condensations a) and b)) or with a secondary amine

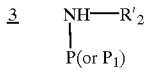

(for condensation a)), these amine derivatives being respectively chosen, according to $R_1$ structure, among the groups where —NH—$R'_2$ or

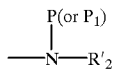

correspond to the following entities: —X—B—Y—(C—Z)$_{x2}$, —Y—(C—Z)$_{x2}$, —Z or —W, (WA)$_{x1}$—X—, and (W—A)$_{x1}$—X—B—Y, in which one out of W, A, X, B, Y, C and Z is substituted by a nitrile group —(CH$_2$)$_x$—CN, x having the same meaning as indicated above.

After the condensation step and the eventual reduction step, the nitrile group is hydrolyzed to yield the carboxylate function —COOH that could further be reacted to lead to a —COR function.

As an illustration, the amine derivatives $H_2N$—$R'_2$ and

can be obtained in the following manner, hereafter called condensation β: condensation of the acrylonitrile with a primary amine $R_4$—$NH_2$ in which $R_4$ represents one of the entities X—B—Y—C, Y—C—, —B—Y, —A—X—B—Y, according to the following scheme:

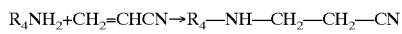

When $R_4$ represents a primary amine $H_2N$—$R_5$—, the $NH_2$ function being eventually protected by a group like tosyle, mesityle or phtalimide and revealed after condensation with acrylonitrile and when $R_5$ represents one of the entities —B—Y—C, —C—, —B—, —A—X—B—, the amount of diamine $NH_2$—$R_{5—NH2}$ used in the above reaction must be in excess compared to the acrylonitrile, the molar ratio acrylonitrile/diamine being of 1:3 in order to obtain the nitrile $H_2N$—$R_5NH$—$CH_2$—$CH_2$—CN.

It is noticeable that the condensation β of the acrylonitrile with an amine $R_4$—$NH_2$, followed by the hydrolysis of the nitrile function, also called γ, to lead to the carboxylate function, also permits the synthesis of a compound of this invention if the starting amine derivative possess 4 nitrogenated functions.

Compounds of this invention can also be prepared starting from a dinitrile such as the dinitrile NC—A—X—B—Y—C—CN which, after hydrogenation, leads to the compound of formula $H_2N$—$CH_2$—A—X—B—Y—$CH_2$—$NH_2$. As an illustration, an especially interesting dinitrile can be obtained by condensation, hereafter called condensation δ, of the acrylonitrile on a diamine of formula $NH_2$—B—$NH_2$, the acrylonitrile being in excess compared to the diamine, the molar ration acrylonitrile/diamine being of the order 3:1, such condensation leading to the dinitrile of formula NC—(CH$_2$)$_2$—NH—B—NH—(CH$_2$)$_2$—CN.

The supplementary step of hydrogenation of the dinitrile in the presence of Raney nickel leads to the formation of a compound of this invention of formula: $H_2N$—(CH$_2$)$_3$—NH—B—NB—(CH$_2$)$_3$—$NH_2$.

If needed, before the hydrogenation step, the dinitrile may be reacted with an halide $R_1$—Z, where $R_1$ and Z have the same meaning as above, or with an acid or ester halide according to condensation α, in order to introduce a coordinative function such as —COR, on the dinitrile.

c) An other condensation can be used for the synthesis of the compounds of this invention which is the reaction of one or two compounds 1 of formula $R_1$—Z, where $R_1$ represents W—A, W—A—X—B, X—B—, —B—Y, —B—Y—C—Z, with a piperazinone, followed by the hydrolysis of the amide function.

This condensation leads either to a monosubstitution according to:

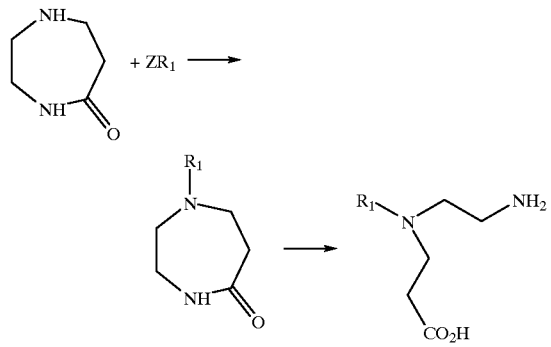

or to a disubstitution according to:

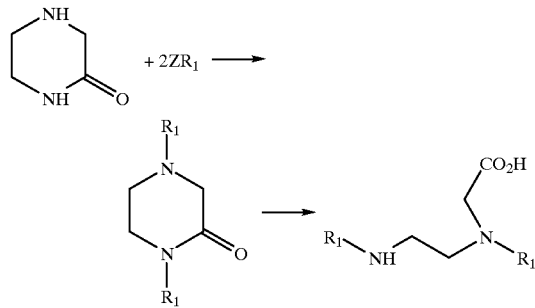

d) In order to obtain the cyclic derivatives of formula IIa, mono-substituted, a condensation is used where a compound 5 that possess two primary amine functions as in $H_2N$—$T_1$—$R_9$—$T_2$—$NH_2$, is reacted with a dialdehyde 6 of formula OHC—$T_1$—$R_{10}$—$T_{2—CHO, T1}$ and $T_2$, identical or different, being an alkyl chain —(CH$_2$)$_x$ in which x represents an integer varying from 1 to 3, substituted or not by one or several groups P or by one or several groups $P_1$, P and $P_1$ being as defined above, $R_9$ and $R_{10}$, identical or different, having the same meaning as the one indicated for X and Y when y=1.

The cyclic product of this reaction is then reduced.

In order to prepare the diamine 5, a dinitrile of formula NC—T$_1$—R$_9$—T$_2$—CN is advantageously used and reduced.

The reduction step is realized in the presence of a hydrogenation catalyst, sometimes, if needed, under pressure.

Satisfactory results are obtained by using hydrogen gas. The catalyst may be, as an example, Raney nickel.

The use of the dinitrile reactant is an efficient way to introduce the desired substituents along the chain.

In order to facilitate the reaction of the dialdehyde with the diamine, a coupling agent may be advantageously used. Among such appropriate agents, one can mention the hexahydrate nickel chloride as an example.

For the reduction step, a reducing agent is used in the presence of a hydrogenation catalyst.

A synthesis method of a cyclic derivative of this invention will be reported in details in the preparation examples that follow.

The above defined compounds can form metal complexes that are capable of reversible dioxygen binding.

This invention relates then to metal complexes, and also to their hydrates, that are formed by association of the polynitrogenated compounds of this invention, as defined above, and a metal.

The metals that are appropriate for the preparations of the metal complexes of this invention, are transition metals, and more specifically cobalt, chromium, iron, manganese, ruthenium, rhodium, copper, nickel, palladium, osmium and platinum.

The preferred transition metals are chosen among cobalt, copper, nickel, manganese and iron.

In the metal complexes of this invention, the transition metals above mentioned are in a reduced form; their valence states are +2 or +1 before reaction with $O_2$.

The metal complexes used in this invention are then positively charged. Their charge is balanced by a counter-ion; this anion is inert towards chemical or electrochemical reactions that can be used for the desorption of $O_2$, for the transport or the regeneration. Especially appropriate anions are chosen among halides, sulfates, phosphates, nitrates, carbonates, perchlorates, tetrafluoroborates and hexafluorophosphates.

The halides are preferably bromide or chloride ions. They may also be iodide or fluoride ions.

The anions may also be organic anions as acetates, citrates, triflates or methylsulfonates.

Advantageously, such metal complexes present a solubility, in aqueous media, greater or equal to 0.5 M, and preferably of the order of 1 M.

At a concentration of 1 M, the viscosity of the aqueous solution of these complexes is less than twice the viscosity of water.

The metal complexes are capable of binding dioxygen when they are contacted to a gas mixture that contains dioxygen at an advantageous partial pressure of the order of 0.2 bar, that is at the atmospheric partial pressure, especially at the temperature of 15° C.

The diffusion coefficient value of these complexes in the medium does not exceed five times the diffusion coefficient value of the dioxygen dissolved in that same medium.

The lifetime of these complexes is advantageously greater than one month and can reach one year or more.

In order to prepare these complexes, one advantageously reacts a metal salt with a polynitrogenated compound of this invention. These metal salts can be acetates, nitrates, halides or sulfates. The reaction is advantageously carried out in aqueous solutions. Equimolar amounts of polynitrogenated compounds and metal salts are used.

According to the pH of the solution and also according to the favored coordination arrangement of the metal, several different equilibria are observed that involve the polynitrogenated compound, also called ligand, the metal ion and the metal complex If LH designates the neutral form of the ligand and $M^{2+}$ designates the metal, the following equilibria are observed among others:

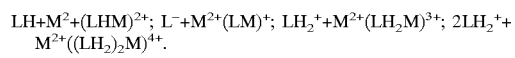

To each equilibrium corresponds an equilibrium constant, also called metallation constant.

The amount of complex formed is dependent on the temperature of the solution, on the ratio of the initial concentrations of both reactant entities, and on the pH of the solution.

The pH of the solution is a very important factor that determines the reactivity of the ligand with the metal ion. Indeed, if the amine functions are protonated, they only have a weak interaction with the metal, while if they are unprotonated, they fully participate to the coordination of the metal. Then, preferred forms of the compounds of this invention are the LH and L$^-$ forms. The choice of the right pH for the preparation of the metal complex will then be made for each compound by evaluating at first the protonation constants of the ligand.

The study, made by the inventors, of the metal complexes of compounds of formula I and α, shows their capacity to reversibly bind molecular oxygen.

Because of their stereochemistry, the number and the combination of electron-donating groups (the coordination functions), and of electron-withdrawing groups (halides, nitro, alcoxy), all these metal complexes, from now on designated as complex II and Cp, are especially well adapted for carrying dioxygen. They present advantageously an affinity constant for molecular oxygen in the range $10^4$ to $10^7$ $M^{-1}L$ and have a lifetime greater than one month after oxygenation in aqueous media.

It is interesting to note that the affinity constant of the compound of formula:

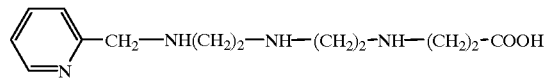

is $10^7$ $M^{-1}L$ while the corresponding compound that possess a pyridyl group instead of the carboxylate moiety, has an affinity constant of $10^{11}$ $M^{-1}L$ (MARTELL et al, J. Chem. Soc. Chem. Commun. (1984), 335–).

This result outlines the interest of having a carboxylate group or a related —COR group in the compounds of this invention.

This invention relates also to a process for the separation and the production of dioxygen, from a gas mixture, that utilises such complexes II or their salts or their hydrates, as defined above. The process of this invention comprises three main steps:

the absorption step where a metal complex II in aqueous solutions or partially aqueous solutions is contacted with a gas mixture in such conditions that the oxygen contained in the gas mixture is bound and leads to the formation of a dimer of formula CpO$_2$Cp in which Cp represents a metal complex molecule.

the desorption step where the bound dioxygen is unloaded, this step being carried out in a different compartment than the absorption compartment.

the recovery of the unloaded dioxygen.

In the absorption step the metal complex II is in an aqueous or partially aqueous solution at concentrations of 0.1 to 1 M, at pH 6 to 12 and preferably from 7 to 9. The complex may be generated in situ by adding the polynitrogenated ligand and a metal salt in an aqueous or partially aqueous medium.

Partially aqueous solutions are mixtures of water with an organic solvent that is miscible to water. Examples of such organic solvents are alcoholic solvents like methanol and ethanol or amide solvents such as the dimethylformamide.

The metal complex in aqueous or partially aqueous solution may also be immobilized on a hydrophilic membrane that is permeable to dioxygen. This membrane is made of a polymer such as polysulfone, polyamide, polyester, polyolefin, polycarbonate, halogenated polyorganosilane, polyorganosiloxane, polyvinyl and polyimide.

One side of the membrane is contacted with the gas mixture containing dioxygen, then unloading of the bound dioxygen being realised on the other side of the membrane.

The desorption of the bound dioxygen is effected by using the vacuum, for example, that is to say that the dioxygen partial pressure in the atmosphere in equilibrium with the solution, is decreased from 0.2 to 0.03 bar. When the metal complex in solution is immobilized on a membrane, the partial pressure may be decreased and/or a temperature gradient applied between the two sides of the membrane.

Partial pressure gradient between the two sides of the membrane may be of 0.1 bar and the temperature gradient of 10° C., as examples.

Another mean of unloading dioxygen is the electrochemical oxidation of the $CpO_2Cp$ dimer by applying an appropriate potential between two electrodes of an electrochemical cell.

The binding of dioxygen by a metal complex in aqueous solution is described by the following equilibria, where Cp represents the metal complex:

$Cp+O_2 \rightleftharpoons CpO_2$ $CpO_2+Cp \rightleftharpoons CpO_2Cp$

The dimer $CpO_2Cp$ is the main oxygenated species resulting from the reaction of $O_2$ with the metal complex in aqueous solution.

Such dimers are also part of the invention.

References will be made hereafter to FIGS. 1 to 4 where:

FIG. 1: the absorption capacity of ligand L7 complexed to the $Co^{2+}$ ion is represented in percentage as a function of the pH of the solution of $(L7)Co^{2+}$ complex before introduction of dioxygen. The amount of dioxygen absorbed is measured by volumetry.

Figure 2:
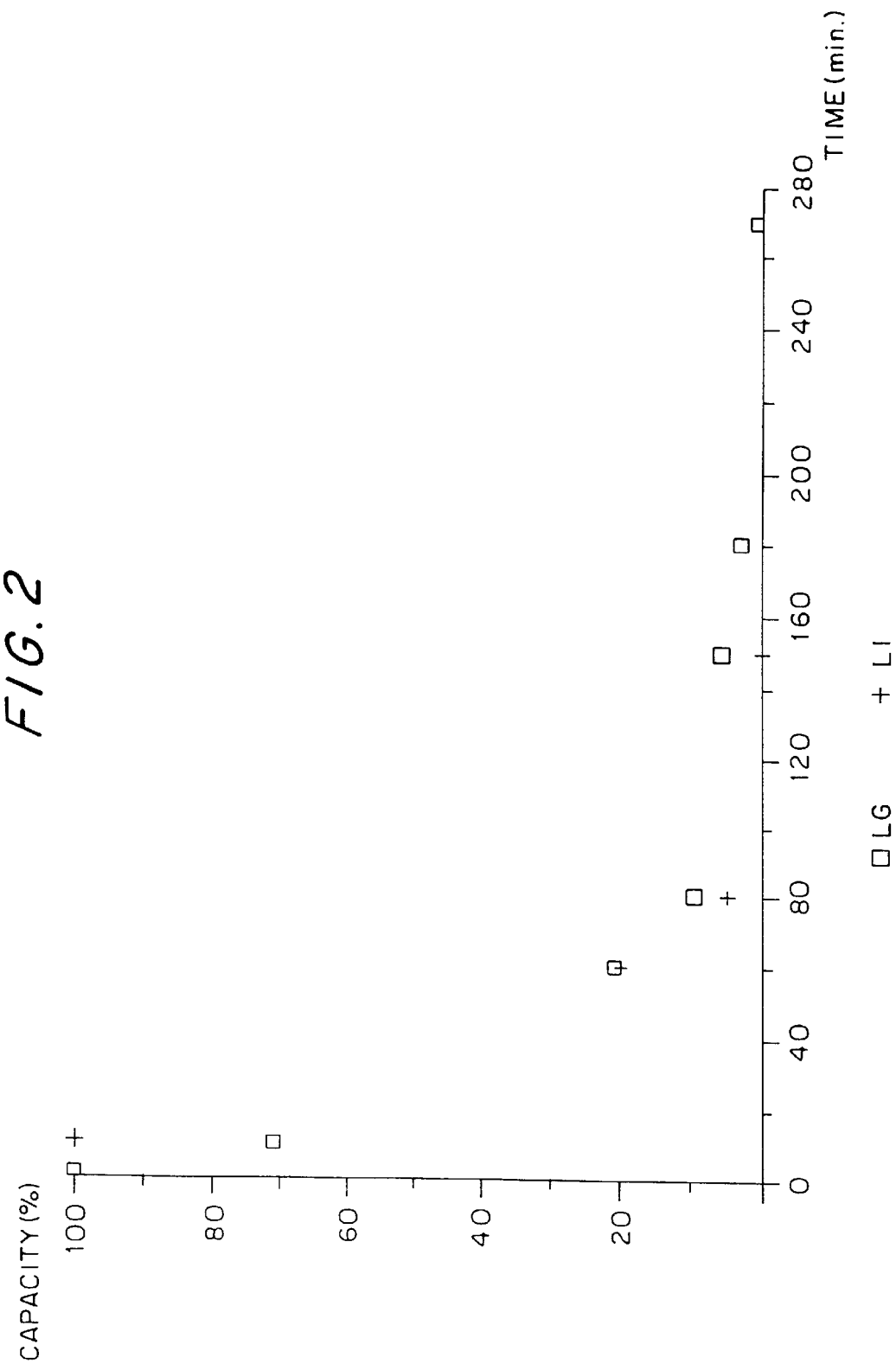

FIG. 2: the decrease of the $O_2$ absorption capacity (or degradation), of the linear pentadentate complexes of cobalt is represented as a function of time.

Figure 3:
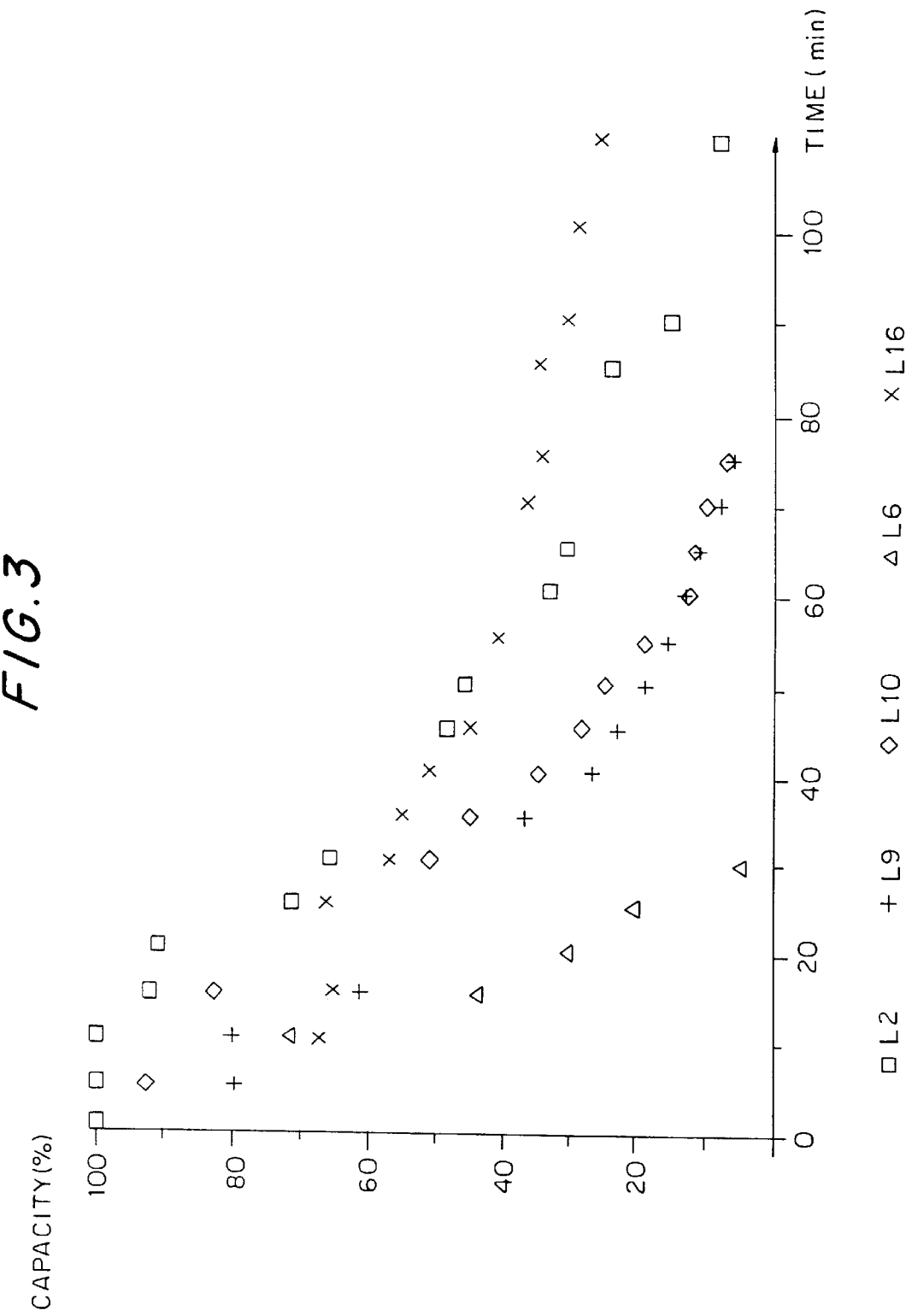

FIG. 3: the decrease of the $O_2$ absorption capacity of linear tetradentate complexes of cobalt or non linear pentadentate complexes of cobalt is represented as a function of time.

Figure 4:
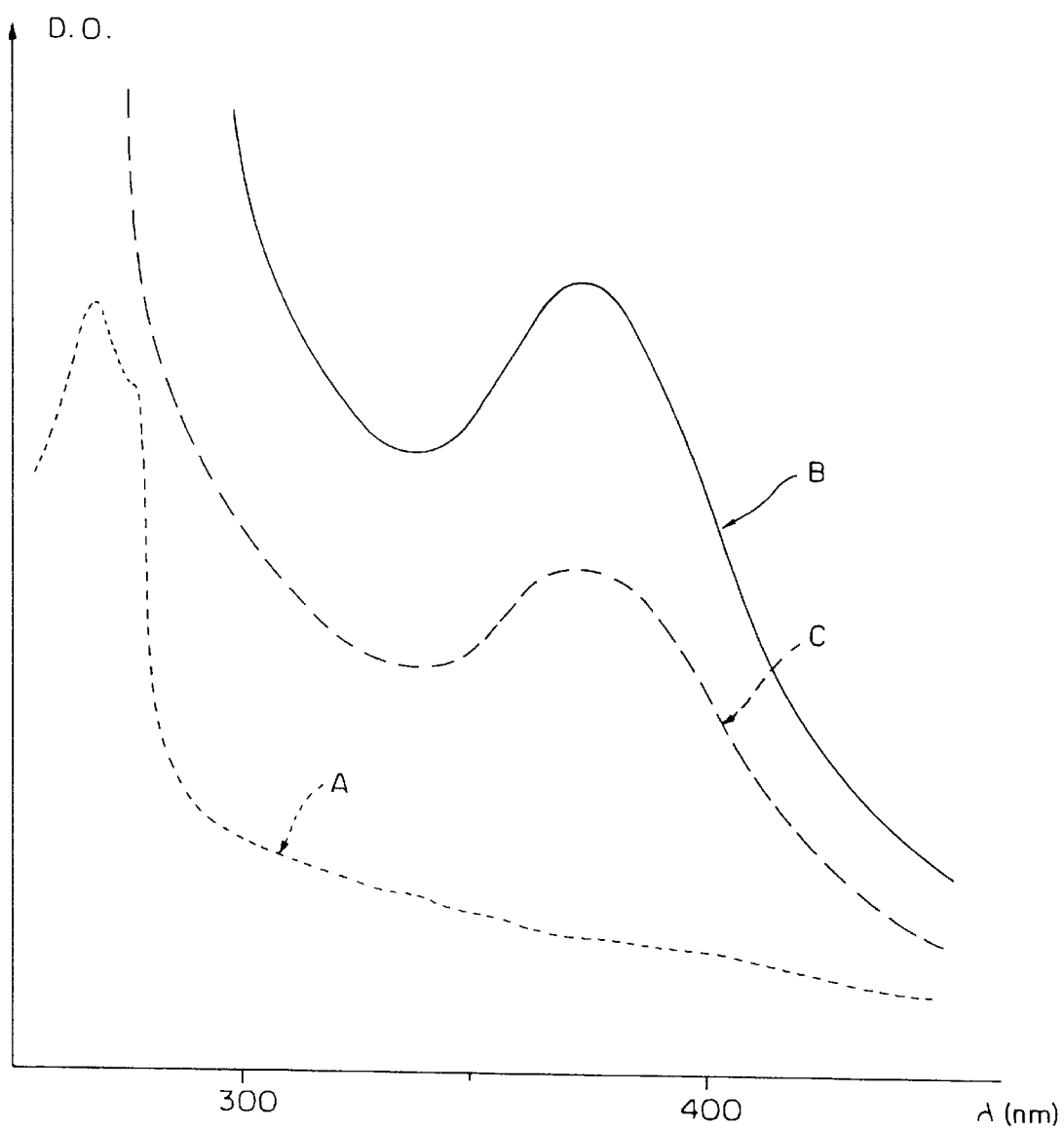

FIG. 4: the intensity of the charge transfer band of dioxygen is plotted:
curve A represents the UV-Visible spectrum of ligand L6
curve B represents the UV-Visible spectrum of the complex $(L6)CoO_2Co(L6)$ under dioxygen atmosphere,
curve C represents the UV-Visible spectrum of the solution of curve B, after nitrogen bubbling.

The following examples illustrate the synthesis of the polynitrogenated compounds of this invention according to one of the condensations described above, as well as the conditions used for the absorption of dioxygen by a metal complex of this invention and the desorption of this dioxygen. Of course, this invention is not limited to these examples.

1) Examples 1a and 1b illustrates the particular case of the preparation of a compound of this invention by using the condensation β followed by the hydrolysis γ.

EXAMPLE 1a

Synthesis of Compound of Formula L1

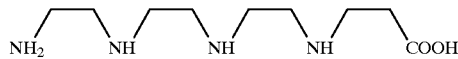

1st step: nitrile preparation by condensation β.

To 10 mL of acrylonitrile (0.152 mole) (JANSSEN CHIMICA, ref. 14963.25), are added 60 g of triethylenetetramine (0.41 mole) (JANSSEN CHIMICA, ref. 15792.78), during about 30 minutes. The resulting blue solution is then stirred at room temperature during 24 hours. The excess of triethylenetetramine is removed by distillation under reduced pressure (0.1 mmHg) and the remaining liquid is used without further purification.

2nd step: nitrile hydrolysis into acid according to reaction α

The resulting nitrile is maintained under reflux during 10h30 in 100 mL of water and 50 mL of concentrated sulfuric acid (d=1.83). After cooling and concentrating, the acid is precipitated by adding acetone and cooling. The precipitate is filtered and washed with acetone. The resulting solid is recrystalized in a water/sulfuric acid/acetone mixture. After filtration, the solid is washed with acetone and then dried. 15 g of acid are collected as a white powder.

$^1H$ NMR ($D_2O$): δ 2.88(t,2H), 3.41(t,2H), 3.51(m,12H).

Following a similar operating mode, the compoud of formula L'1

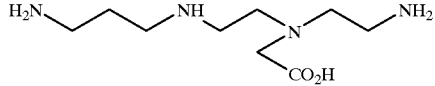

is obtained by condensation of the compound of formula

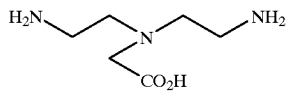

with acrylonitrile, followed by an hydrolysis.

2) Examples 2a to 2j illustrate the synthesis of compounds of this invention according to condensation b) by reaction of an aldehyde with a primary amine, $R'_2$—$NH_2$ that possess a nitrile group. These examples 2a to 2j have in common the first step which is the synthesis of the nitrile of formula $N_1$

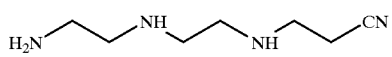

The preparation of the nitrile $N_1$ is carried out by condensation β in the following manner:
to 0.304 mole of acrylonitrile are added 0.92 mole of diethylene triamine (JANSSEN CHIMICA Ref. 11431.82)

during about 1 hour. The bulk medium is then stirred at room temperature for 48 hours. The excess of diethylenetriamine is removed by distillation under reduced pressure (0.1 mmHg). The resulting yellow liquid is used without further purification.

EXAMPLE 2a

Synthesis of Compound of Formula L2

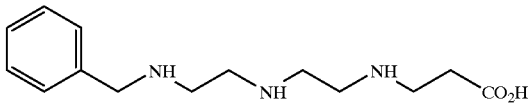

1st step: preparation of the nitrile $N_1$.
2nd step: condensation of nitrile $N_1$ with benzaldehyde and reduction of the imine.

A mixture of 7.8 g of the nitrile $N_1$ (0.05 mole) and 5.1 mL of benzaldehyde (0.05 mole) (JANSSEN CHIMICA, ref. 10522.46) is heated under reflux during 30 minutes, in 40 mL of ethanol. After evaporation of the alcohol, the product is hydrogenated in the presence of 1g Pd/C at 10% in 60 mL of ethanol, previously degassed during 4 days. The catalyst is then removed by filtration and the filtrate is evaporated to dryness. The resulting orange oil is used without further purification.
3rd step: Hydrolysis of the nitrile obtained at the previous steps into acid.

The orange oil is heated under reflux during 2h30 in 120 mL of water and 25 mL of concentrated sulfuric acid (d=1.83). The acid is precipitated by adding acetone and cooling during one day at −15° C. The precipitate is filtered and then recrystallized in a water/sulfuric acid/acetone mixture.

After filtration, washing with acetone and drying, 2.74 g of acid are collected as a white powder.
$^1$H NMR (D$_2$O): δ 2.87(t,2H), 3.40(t,2H), 3.53(t,8H), 4.42(s,2H); 7.5(s,5H).

The elemental analysis of the obtained solid reveals the presence of two sulfuric acid molecules and one water molecule by molecule of compound 2.

EXAMPLE 2b

Synthesis of Compound of Formula L3

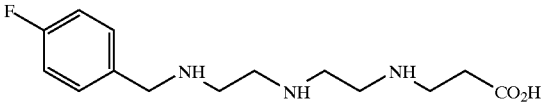

1st step: synthesis of the nitrile $N_1$
2nd step: condensation of nitrile $N_1$ on the 4-fluoro, benzaldehyde and reduction of the imine.

During 25 minutes, 7.3 g of nitrile $N_1$ (0,047 mole) and 5.8 g of 4-fluorobenzaldehyde are heated under reflux in 20 mL of ethanol. After evaporation of the alcohol, the product is hydrogenated during 4 days with 1,5 g Pd/C at 10% in 40 mL of degased pure ethanol. The catalyst is then removed by filtration and the filtrate is evaporated to dryness. The product is precipitated as a hydrochlorate by adding 80 mL of hydrochloric acid 6 N. The white solid formed is collected by filtration and then recrystallized in 90% ethanol. After filtration and drying, 11 g of product are collected as a white powder.

$^1$H NMR (D$_2$O): δ 3.03(t, 2H, CH$_2$CN); 3.52(m, 10H, NH—CH$_2$—CH$_2$—NH, CH$_2$CH$_2$—CN); 4.31(s, 2H, CH$_2$—C$_6$H$_4$F); 7.21(t, 2H, H$_2$-phenyl) 7.49(m, 2H, H$_3$-phenyl).
3rd step: hydrolysis of the nitrile previously obtained into an acid.

During 1 hour, 7.8 g of the nitrile obtained at the second step (0.021 mole) in 50 mL of water and 30 mL of concentrated sulfuric acid (d=1.83) are heated under reflux. The acid is precipitated by adding ethanol and cooling at −15° C. during two days. After filtration, washing with ethanol and drying, 8 g of acid are collected as a white powder.
$^1$H NMR (D$_2$O): δ 2.87(t, 2H, —CH$_2$—COOH); 3.39(t, 2H, —CH$_2$—CH$_2$—COOH); 3.53(s, 8H, NH—CH$_2$CH$_2$—NH); 4.3(s, 2H, CH$_2$—C$_6$H$_4$F); 7.2(t, 2H, H$_2$—Phenyl); 7.51(m, 2H, H$_3$—Phenyl).

EXAMPLE 2c

Synthesis of Compound of Formula L4

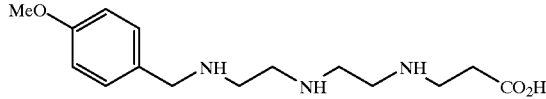

1st step: preparation of the nitrile $N_1$.
2nd step: condensation of the nitrile $N_1$ with the 4-methoxy benzaldehyde and reduction of the imine.

During 20 minutes 8 g of nitrile $N_1$ (0.051 mole) and 6.2 g of 4-methoxybenzaldehyde are heated under reflux in 20 mL of pure ethanol. After evaporation of the alcohol, the product is hydrogenated during five days with 1.5 g Pd/C at 10% in 40 mL of degased pure ethanol. The catalyst is removed by filtration and the filtrate is evaporated to dryness. The product is precipitated as a hydrochlorate by adding 80 mL of hydrochloric acid 6N and cooling at −15° C. during four days. A white solid is collected by filtration and washed with pure ethanol. After drying, 11 g of product are collected as a white powder.
$^1$H NMR(D$_2$O): δ 3.02(t, 2H, CH$_2$—CN); 3.47(m, 10H, NHCH$_2$CH$_2$NH, CH$_2$CH$_2$CN); 3.85(s, 3H, CH$_3$—OC$_6$H$_4$); 4.26 (s, 2H, CH2—C$_6$H$_4$OMe); 7.06(d, 2H, H$_2$-Phenyl); 7.43(d, 2H, H3-Phenyl).
3rd step: hydrolysis of the nitrile into an acid.

During one hour, 3.43 g of the nitrile obtained in the 2nd step (0.009 mole) are heated under reflux in 30 mL water and 15 mL of concentrated sulfuric acid (d=1.83). The acid is precipitated by adding ethanol and cooling at −15° C. during one night. After filtration, washing with ethanol and drying, 2.9 g of acid are collected as a grey powder.
$^1$H NMR(D$_2$O): δ 2.87(t, 2H, —CH$_2$—COOH; 3.40(t,2H, —CH$_2$—CH$_2$ COOH); 3.52(m, 8H, NH—CH$_2$CH$_2$—NH); 3.84(s, 3H, CH$_3$—OC$_6$H$_4$); 4.26(s, 2H, CH$_2$—C$_6$H$_4$OMe); 7.07(s, 2H, H$_2$-phenyl); 7.46(d, 2H, H$_3$-phenyl).

EXAMPLE 2d

Synthesis of Compound of Formula L5

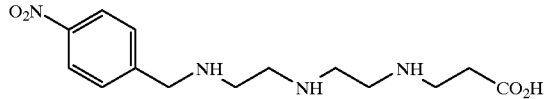

1st step: preparation of the nitrile $N_1$.
2nd step: condensation of the nitrile $N_1$ with the 4-nitrobenzaldehyde and reduction of the imine.

During 30 minutes, 8 g of nitrile $N_1$ (0.051 mole) and 6.2 mL of 4-nitrobenzaldehyde (0.051 mole) are heated under reflux in 20 mL of pure ethanol. After evaporation of the alcohol, the product is hydrogenated during five days with 1.5 g of Pd/C at 10% in 40 mL of degased pure ethanol. The catalyst is removed by filtration and the filtrate is evaporated to dryness. The product is precipitated as an hydrochlorate by adding 80 mL of hydrochloric acid 6N and cooling at −15° C. during four days. The white solid is collected by filtration and washed with pure ethanol. After drying, 9.5 g of product are collected as a whitish powder.

3rd step: hydrolysis of the nitrile into an acid.

During 1h30, 9.5 g of the nitrile obtained in the second step (0.009 mole) in 30 mL water and 20 mL of concentrated sulfuric acid (d=1.83) are heated under reflux.

The acid is precipitated by adding ethanol and cooling at −15° C. during one night. After filtration, washing with ethanol and drying, the acid is collected as a grey powder. After recrystallization in an ethanol/water/sulfuric acid mixture followed by drying, 4.7 g of acid are collected as a white powder.

$^1$H NMR($D_2O$): δ 2.87(t, 2H, $CH_2COOH$); 3.40(t, 2H, $CH_2CH_2COOH$); 3.53(t, 8H, NH—$CH_2CH_2$NH$CH_2CH_2$NH); 4.42(s, 2H, $C_4H_4N$—$CH_2$); 7.42(d, 2H, $H_5$—Ph, $H_3$—Ph); 7.61(d, 2H, $H_2$—Ph, $H_6$—Ph);

EXAMPLE 2e

Synthesis of Compound of Formula L6

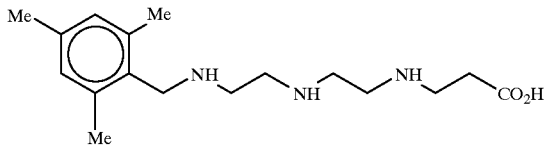

1st step: preparation of the nitrile $N_1$.

2nd step: condensation of the nitrile $N_1$ with the mesitaldehyde and reduction of the imine.

During 30 minutes, 7.8 g of the nitrile $N_1$ (0.05 mole) and 7.4 mL of mesitaldehyde (0.05 mole) are heated under reflux in 40 mL of pure ethanol. After evaporation of the alcohol, the product is hydrogenated with 1 g of Pd/C at 10% in 60 mL of degased pure ethanol during 4 days. The catalyst is removed by filtration and the filtrate is evaporated to dryness. The orange oil obtained is used without further purification.

3rd step: hydrolysis of the nitrile into acid.

The oil obtained in the second step is heated under reflux during 2h30 in 50 mL of water and 25 mL of concentrated sulfuric acid (d=1.83). The acid is precipitated by adding acetone and cooling during one day at −15° C. The precipitate is filtered and recrystallized in a mixture of sulfuric acid diluted at 5% and ethanol. After filtration, washing with acetone and drying, 3.8 g of acid are collected as a white powder.

$^1$H NMR($D_2O$); δ 2.27(s, 3H, $CH_3$—Ph); 2.38(s, 6H, $CH_3$—Ph); 2.88(t, 2H, $CH_2COOH$); 3.42(t, 2H, $CH_2CH_2COOH$); 3.54–3.65(m, 8H, NH—$CH_2CH_2$—NH); 4.40(s, 2H, $CH_2$—Ph); 7.04(s, 2H, 4—Ph).

EXAMPLE 2f

Synthesis of Compound of Formula L7

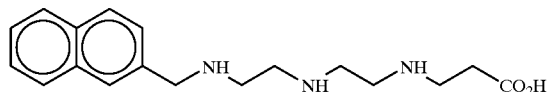

1st step: preparation of nitrile $N_1$.

2nd Step: condensation of the nitrile $N_1$ with the 2-naphtaldehyde and reduction of the imine.

During 30 minutes, 7.8 g of nitrile $N_1$ (0.05 mole) and 7.8 mL of 2-naphtaldehyde (0.05 mole) are heated under reflux in 40 mL of pure ethanol. After evaporation of the alcohol, the product is hydrogenated with 1 g of Pd/C at 10% in 60 mL of degased pure ethanol during four days. The catalyst is removed by filtration and the filtrate is evaporated to dryness. The resulting orange oil is used without further purification.

3rd step: hydrolysis of the nitrile into an acid

The oil obtained during the second step is heated under reflux during 1h30 in 60 mL water and 25 mL of concentrated sulfuric acid (d=1.83). The acid is precipitated by adding acetone and cooling during one day at −15° C. The precipitate is filtered and recrystallized in a mixture water/sulfuric acid/ethanol. After filtration, washing with acetone and drying, 4.2 g of acid are collected as a white powder.

$^1$H NMR($D_2O$): δ 2.86(t, 2H, $CH_2$—COOH); 3.375(t, 2H, $CH_2CH_2$—COOH); 3.55(m, 8H, NH—$CH_2CH_2$—NH); 4.5 (s, 2H, $CH_2$-napht); 7.61(m, 3H, H-napht); 8.02(m, 4H, H-napht).

EXAMPLE 2g

Synthesis of Compound of Formula L8

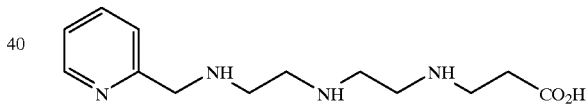

1st step: preparation of nitrile $N_1$.

2nd step: condensation of the nitrile $N_1$ and 2-pyridine carboxaldehyde and reduction of the imine.

During 30 minutes, 8.2 g of nitrile (0.052 mole) and 5 mL of 2-pyridine carboxaldehyde (JANSSEN CHIMICA, ref. 13182.87) are heated under reflux, in 40 mL of pure ethanol. After evaporation of the alcohol, the product is hydrogenated in the presence of 1 g of Pd/C catalyst at 10% in 40 mL of ethanol previously degassed during 4 days. The catalyst is then filtered and the filtrate is evaporated to dryness. The remaining orange oil is used without further purification.

3rd step: hydrolysis of the nitrile into acid.

The oil obtained in the second step is heated under reflux during 7h30 in 200 mL of water and 50 mL of concentrated sulfuric acid (d=1.83). The acid is precipitated by adding acetone and cooling at −15° C. during 2 days. The precipitate is filtered and recrystallized in a water/sulfuric acid/acetone mixture. After filtration, the solid is washed with acetone, dried, and 10 g of acid are collected as a whitish powder.

$^1$H NMR ($D_2O$): δ 2.89(t,2H), 3.42(t, 2H), 3.6(m,8H), 4.63(s,2H), 7.87(t,1H), 7.96(d,1H), 8.37(t;1H), 8.77(d,1H).

EXAMPLE 2h

Synthesis of Compound of Formula L9

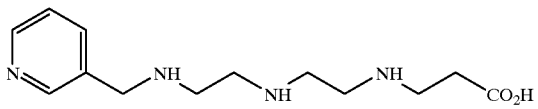

1st step: preparation of nitrile $N_1$.

2nd step: condensation of nitrile $N_1$ with the 3-pyridine carboxaldehyde and reduction of the imine.

During 30 minutes, 7.8 g of nitrile $N_1$ (0.05 mole) are heated under reflux in 4.7 mL of 3-pyridine carboxaldehyde and 40 mL of pure ethanol. After evaporation of the alcohol, the product is hydrogenated with 1 g of Pd/C at 10% in 40 mL of pure ethanol degassed during 4 days. The catalyst is removed by filtration and the filtrate is evaporated to dryness. The resulting orange oil is used without further purification.

3rd step: hydrolysis of the nitrile into an acid.

The oil obtained in the second step is heated under reflux during 2h30 in 120 mL of water and 25 mL of concentrated sulfuric acid (d=1.83). The acid is precipitated by adding acetone and cooling during one day at −15° C. The whitish precipitate is filtered and recrystallized in a mixture of sulfuric acid diluted at 5% and ethanol. After filtration, washing with acetone and drying, 2.5 g of acid are collected as a white powder.

$^1$H NMR($D_2O$): δ 2.87(t, 2H, $CH_2COOH$); 3.39(t, 2H, $CH_2CH_2COOH$); 3.56–3.67(m, 8H, NH—$CH_2CH_2$—NH—$CH_2CH_2$—NH); 4.61(s, 2H, $C_4H_4N$—$CH_2$); 8.17(t, 1H, $H_5$—Py); 8.81(d, 1H, $H_4$—Py); 8.88(d, 1H, $H_6$Py); 9.05(s, 1H, $H_2$—Py).

EXAMPLE 2i

Synthesis of Compound of Formula L10

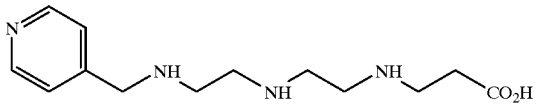

1st step: preparation of the nitrile $N_1$.

2nd step: condensation of the nitrile $N_1$ with the 4-pyridine carboxaldehyde and reduction of the imine.

During 30 minutes, 7.8 g of the nitrile $N_1$ (0.05 mole) are heated under reflux in 4.77 mL of 4-pyridine carboxaldehyde (0.05 mole) and 40 mL of pure ethanol. After evaporation of the alcohol, the product is hydrogenated in the presence of 1 g Pd/C at 10% in 60 mL of degassed pure ethanol, during 4 days. The catalyst is removed by filtration and the filtrate is evaporated to dryness. The resulting orange oil is used without further purification.

3rd step: hydrolysis of the nitrile into an acid.

The oil obtained in the second step is heated under reflux during 1h30 in 120 mL of water and 25 mL of concentrated sulfuric acid (d=1.83). The acid is precipitated by adding acetone and cooling during one day at −15° C. The precipitate is filtered and recrystallized in a mixture of water, sulfuric acid and ethanol. After filtration, washing with acetone and drying, 2.3 g of acid are collected as a white powder.

$^1$H NMR ($D_2O$): δ 2.88 (t, 2H, $CH_2$—$CO_2H$); 3.41 (t, 2H, $CH_2$—$CH_2$—$CO_2H$); 3.55–3.70 (m, 8H, N—$CH_2$—$CH_2$—NH—$CH_2$—$CH_2$—NH); 4.67 (s, 2H, $C_4H_4N$—$CH_2$); 8.23 (d, 1H, $H_3$—Py); 8.23 (d, 1H, $H_5$—Py); 8.89 (d, 1H, $H_2$—Py); 8.89 (d, 1H, $H_6$—Py)

EXAMPLE 2j

Synthesis of Compound of Formula L11

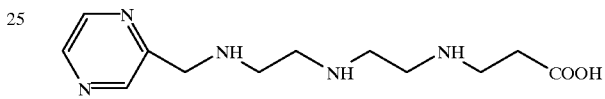

1st step: preparation of the nitrile $N_1$.

2nd step: condensation of the nitrile with 2-pyrimidine carboxaldehyde and reduction of the imine.

The nitrile (0.05 mole) is heated under reflux with 0.05 mole of 2-pyrimidine carboxaldehyde in 50 mL of ethanol, during 20 to 30 minutes. After evaporation of the alcohol, the product is hydrogenated during 3 to 5 days in the presence of 2 g of Pd/C catalyst at 10% in 50 mL of previously degassed ethanol. The catalyst is removed by filtration and the filtrate is evaporated to dryness.

The resulting oil is used without further purification.

3rd step: hydrolysis of nitrile into acid.

The obtained oil is heated under reflux during 1 to 2 hours in 60 to 120 mL of water and 30 to 60 mL of concentrated sulfuric acid (d=1.83). The acid is precipitated by adding ethanol and cooling for 1 to 4 days. The precipitate is filtered and recrystallized in a water/sulfuric acid/alcohol mixture. After filtration, washing with ethanol and drying, the acid is collected as a white powder.

By using the aldehydes and primary amines substituted by a carboxylate function, mentionned in Table I, the following compounds are obtained, following the condensation b).

TABLE I

| Expected Compound | Aldehyde | Primary Amine |
|---|---|---|

TABLE I-continued

| Expected Compound | Aldehyde | Primary Amine |
|---|---|---|
|  | | |

3) The following examples 3a to 3c describe syntheses that are carried out following the same pathway than in the previous examples of 2) and that have in common the first step which is the preparation of the nitrile of formula $N_2$:

$H_2N{\sim}NH{\sim}NH{\sim}NH{\sim}CN$

The preparation of the nitrile $N_2$ is carried out by using the condensation β as follows:
to 0.304 mole of acrylonitrile are added over a period of about one hour, 0.923 mole of triethylenetetramine. The bulk medium is stirred at room temperature during 48 hours.

The excess of triethylenetetramine is removed by distillation under reduced pressure (0.1 mmHg). The remaining yellow liquid is the expected product and is used without further purification.

EXAMPLE 3a

Synthesis of Compound of Formula L12

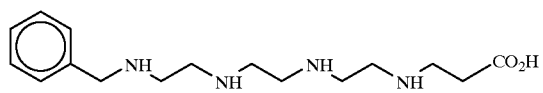

1st step: preparation of the nitrile $N_2$.
2nd step: condensation of the nitrile $N_2$ with the benzaldehyde and reduction of the imine.

During 25 minutes, 9.95 g of nitrile $N_2$ (0.050 mole) is heated under reflux with 5.1 mL of benzaldehyde (0.05 mole) in 40 mL of pure ethanol. After evaporation of the alcohol, the product is hydrogenated during 4 days in the presence of 1.5 g of Pd/C at 10% in 40 mL of degassed pure ethanol. The catalyst is removed by filtration and the filtrate is evaporated to dryness. The product is precipitated as a hydrochlorate by adding 80 mL of hydrochloric acid 6N. The resulting white solid is collected by filtration and then recrystallized in 90% ethanol. After filtration and drying, 13.5 g of product are collected as white powder.

3rd step: hydrolysis of the nitrile into an acid.
During one hour, 6 g of the nitrile prepared in the second step are heated under reflux in 60 mL of water and 30 mL of concentrated sulfuric acid (d=1.83). The acid is precipitated by adding ethanol and cooling at −15° C. during two days. After filtration, washing with ethanol and drying, 8 g of acid are collected as a white powder.

$^1$H NMR (D2O):δ 2.89 (t, 2H,—CH$_2$—CO$_2$H) 3.43 (t, 2H,—CH$_2$—CH$_2$—CO$_2$H) 3.57 (m, 12H, NH—CH$_2$CH$_2$—NH) 4.3 (s, 2H, CH$_2$—Ph) 7.5 (s, 5H, H—Ph)

EXAMPLE 3b

Synthesis of Compound of Formula L13

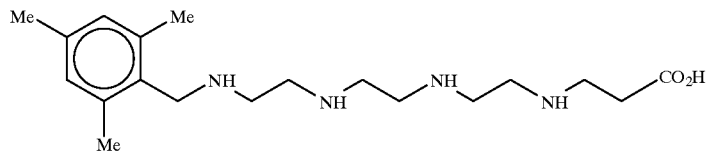

1st step: preparation of Nitrile $N_2$.
2nd step: condensation of the Nitrile $N_2$ with the mesitaldehyde and reduction of the imine into an acid.

During 20 minutes, 10 g of the nitrile $N_2$ (0.05 mole) and 7.5 g of mesitaldehyde (0.05 mole) are heated under reflux in 40 mL of pure ethanol. After evaporation of the alcohol, the product is hydrogenated during five dabs, with Pd/C at 10% in 40 mL of degassed pure ethanol. The catalyst is removed by filtration and the filtrate is evaporated to dryness. The product is precipitated as an hydrochlorate by adding 100 mL of hydrochloric acid 6N and cooling at −15° C. during 4 days. The resulting white solid is collected by filtration and washed with pure ethanol. After drying, 14 g of product are obtained as a white powder.

3rd step: hydrolysis of the nitrile of step 2.
During one hour, 14 g of the nitrile obtained in the previous step are heated under reflux in 100 mL of water and 50 mL of concentrated sulfuric acid (d=1.83). The acid is precipitated by adding ethanol and cooling at −15° C. during one night. After filtration, washing with ethanol and drying, 5.6 g of acid are collected as a grey powder.

$^1$H NMR (D2O):δ 2.26 (S,3H, CH$_3$—Ph) 2.38 (s, 6H, CH$_3$—Ph) 2.88 (t, 2H, CH$_2$—CO$_2$H) 3.41 (t, 2H,—CH$_2$—CH$_2$—CO$_2$H) 3,59 (m, 12H, NH—CH$_2$—CH$_2$—NH) 4.40 (s, 2H, CH$_2$—Ph) 7.04 (s, 2H, H—Ph)

EXAMPLE 3c

Synthesis of Compound of Formula L14

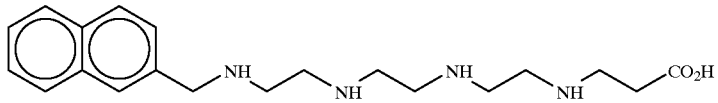

1st step: preparation of the nitrile $N_2$.
2nd step: condensation of the nitrile $N_2$ with the naphtal-2-aldehyde and reduction of the imine.

During 30 minutes, 10 g of the nitrile $N_2$ (0.05 mole) and 7.9 g of 2-naphtalaldehyde are heated under reflux in 40 mL of pure ethanol. After evaporation of the alcohol, the product is hydrogenated during five days with 1.5 g of Pd/C at 10% in 60 mL of degassed pure ethanol. The catalyst is removed by filtration and the filtrate is evaporated to dryness. The product is precipitated as an hydrochlorate by adding 100 mL of hydrochloric acid 6N and then cooling at −15° C. during 4 days.

The white solid collected by filtration is washed with pure ethanol. After drying, 8.6 g of product are collected as a whitish powder.

3rd step: hydrolysis of the nitrile into an acid.

During 1h30, 8.6 g of the nitrile obtained in the second step are heated under reflux in 60 mL of water and 30 mL of concentrated sulfuric acid (d=1.83). The acid is precipitated by adding ethanol and cooling at −15° C. during one night. After filtration, washing with ethanol and drying, the acid is collected as a grey powder. After recrystallization in an ethanol/sulfuric acid mixture, and drying, 5.2 g of acid are collected as a white powder.

$^1$H NMR (D2O):δ 2.88 (t, 2H, $CH_2$—$CO_2H$) 3.42 (t, 2H, $CH_2$—$CH_2$—$CO_2H$) 3.59 (m, 12H, NH—$CH_2$—CH—NH) 4.51 (s, 2H, $CH_2$—napht) 7.64 (m, 3H, H—napht) 8.03 (m, 4H, H—napht)

4) The following examples 4a.1, 4a.2 and 4.b. have in common the first step of their synthesis which is the preparation of the amine of formula $B_1$ following the condensation pattern of b),

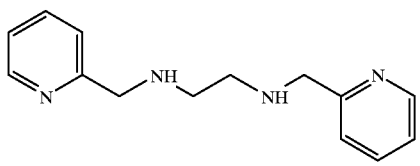

followed by a condensation with an acid halide according to condensation (α).

This first step of preparation of the compound bis-1,6-(pyridyl-2) diaza-2,5-hexane of formula $B_1$ is realized in the following manner:

During 20 minutes, 3.5 mL of ethylenediamine (0.052 mole) (JANSSEN CHIMICA, ref. 11842.08) and 10 mL of 2-pyridine carboxaldehyde are heated under reflux in 40 mL of pure ethanol.

After evaporation of the alcohol, the product is hydrogenated during five days with 1.5 g of Pd/C at 10% in 60 mL of pure ethanol.

The catalyst is removed by filtration and the filtrate is evaporated to dryness. The resulting oil is used without further purification.

$^1$H NMR (D2O): δ 3.63 (s, 4H, NH—$CH_2$—$CH_2$—NH); pH=1 4.66 (s, 4H, $C_4H_4N$—$CH_2$); 7.90 (t, 2H, $H_5$—Py); 7.97 (d, 2H, $H_3$—$_{Py}$); 8.41 (t, 2H, $H_4$—Py); 8.77 (d, 2H, $H_6$—Py);

EXAMPLE 4a1

Synthesis of Compound of Formula L15

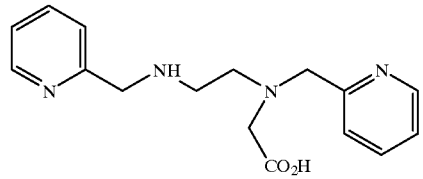

1st step: SYNTHESIS of bis-1,6-(pyridyl-2) diaza-2,5-hexane, $B_1$.
2nd step: Condensation of acrylonitrile with the amine $B_1$.

The amine $B_1$ obtained is heated under reflux in 20 mL of acetonitrile. A solution of 1 mL of acrylonitrile in 10 mL of acetonitrile is then slowly added. The resulting bulk is kept under reflux for 30 minutes and then the solvent is evaporated under reduced pressure. The resulting orange oil is used without further purification.

3rd step: Nitrile hydrolysis into acid.

The oil obtained in the second step is heated under reflux during 1h30 in 20 mL of water and 15 mL of concentrated sulfuric acid (d=1.83).

The solution is concentrated to dryness and then neutralized by a sodium hydroxyde solution up to pH 10. The resulting brown solution is washed four times with 150 mL of chloroform. The orange aqueous phase is concentrated to about 10 mL and then neutralized with 30 mL of hydrochloric acid 6N. The following series of operations is then repeated 4 times: concentration of filtrate, precipitation by adding ethanol, filtration and recovery of the filtrate. All the mineral salts in the solution are thus eliminated. The whitish solid collected after evaporation of the last filtrate solvant is recrystallized in an ethanol/hydrochloric acid 6N mixture. After filtration and drying, 850 mg of acid are collected as thin white needles.

$^1$H NMR($D_2O$): δ 2.9(t,2H, $CH_2$—COOH), 3.37(s, 4H, $CH_2C_5H_4N$), 3.42(t,2H, $CH_2$—$CH_2$—COOH), 3.58–3.72 (m,4H, NB—$CH_2$—$CH_2$—NH), 7.96(t,2H, $H_4$—Pyr), 8.08 (d,2H, $H_3$—Pyr), 8.49(t, 2H, $H_5$—Pyr), 8.82(d,2H, $H_6$—Pyr).

EXAMPLE 4a.2

1st step: synthesis of 1,6-bis (2-pyridyl)-2,5-diazahexane $B_1$.

2nd step: condensation of the bromoethanoic acid with the amine $B_1$.

A solution of 1.16 g of bromoethanoic acid (0.008 mole) and 0.7 g of monohydrated lithium hydroxyde (0.016 mole) in 35 mL of water is added, slowly, over 1h30, to 12 g of the amine B, obtained in the second step and previously heated under reflux in 125 mL of ethanol and 25 mL of water.

The reflux is maintained during 9 hours after the introduction of the reactants. Then the ethanol is evaporated under vacuum. The resulting orange aqueous solution is washed 7 times with 50 mL of dichloromethane. The product is collected by evaporation and then, after protonation by a hydrochloric acid solution at 5% in ethanol, purified by recrystallization in an ethanol/hydrochloric acid at 5% mixture. The expected product is then collected as 1.72 g of a white powder.

$^1$ NMR (D2O): δ 2.57 (t, 2H, NH—$CH_2$—$CH_2$—N—); pH=9 2.70 (t, 2H, NH—$CH_2$—$CH_2$—N—); 3.18 (s, 2H, $CH_2$—$CH_2$—$CO_2H$); 3.72 (s, 2H, $C_4H_4N$—$CH_2$); 3.79 (s, 2H, $C_4H_4N$—$CH_2$'); 7.31 (t, 1H, $H_5$—Py) ; 7.36 (t, 1H $H_5$'—Py); 7.37 (d, 1H, $H_3$—Py); 7.52 (d, 1H, $H_3$'—Py); 7.79(t,1H, $H_4$—Py); 7.84 (t,1H, $H_4$'—Py); 8.38 (d, 1H, $H_6$—Py); 8.43 (d, 1H, $H_6$'—Py);

EXAMPLE 4b

Synthesis of Compound of Formula L16

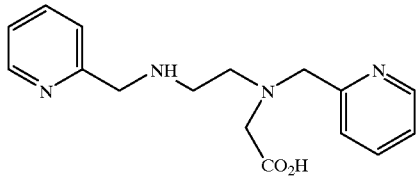

1st step: synthesis of bis-1,6 (pyridyl–2) diaza-2,5-hexane $B_1$.

2nd step: condensation of the 3-bromopropanoic acid with the amine $B_1$.

A solution of 1.27 g of 3-bromo propanoic acid (0.008 mole) and 0.7 g of monohydrated lithium hydroxyde (0.016 mole) in 35 mL of water are added slowly over a period of 2 hours, to a solution of 12 g of amine $B_1$ (0.05 mole) in 125 mL of ethanol and 25 mL of water, under reflux. The reflux is maintained for 9 hours after the reactants addition. The ethanol is evaporated under vacuum. The resulting orange aqueous solution is washed seven times with 50 mL of dichloromethane. The product is collected by evaporation and, after protonation with a 5% hydrochloric acid solution in ethanol, is purified by recrystallization in a mixture of ethanol and hydrochloric acid diluted at 5%. The expected product is collected as 1.94 g of a white powder.

$^1$ NMR (D2O): δ 2.41 (t, 2H, NH—$CH_2$—$CH_2$—N—); pH=9 2.86 (t, 2H, NH—$CH_2$—$CH_2$—N—); 2.88 (t, 2H, $CH_2$—$CH_2$—$CO_2H$); 3.18 (t, 2H, —$CH_2$—$CH_2$—$CO_2H$); 3.82 (s, 2H, $C_4H_4N$—$CH_2$); 4.17 (s, 2H, $C_4H_4N$—$CH_2$'); 7.40 (t, 1H, $H_5$—Py); 7.41 (t, 1H, $H_5$'—Py); 7 43 (d, 1H, $H_3$—Py); 7.46 (d, 1H, $H_3$'—Py); 7.86 (t, 1H, $H_4$—Py); 7.88 (t, 1H, $H_4$'—Py); 8.49 (d, 1H, $H_6$—Py); 8.52 (d, 1H, $H_6$'—Py);

5) The following examples 5a and 5b describe syntheses that are carried out as described in 4) and that have in common the first step which is the preparation of the amine $B_2$.

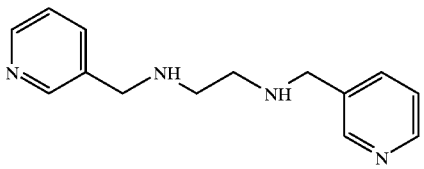

The preparation of this compound of formula $B_2$, the bis-1,6 (pyridyl-3) diaza-2,5-hexane is realized according to:

A mixture of 3.5 mL of ethylenediamine (0.052 mole) and 10 mL of 3-pyridinecarboxaldehyde (0.106 mole) in 40 mL of pure ethanol are heated under reflux for 20 minutes. After evaporation of the alcohol, the product is hydrogenated during five days with 1.5 g of Pd/C at 10% in 60 mL of pure ethanol. The catalyst is removed by filtration and the filtrate is evaporated to dryness. The resulting oil is used without further purification.

EXAMPLE 5a

Synthesis of Compound of Formula L17

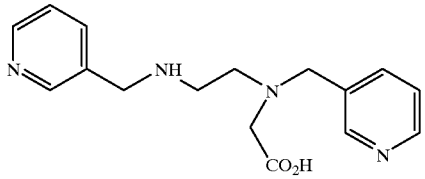

1st step: synthesis of the bis-1,6 (3-pyridyl)-2,5 diaza hexane $B_2$.

A solution of 1.16 g of bromoethanoic acid (0.008 mole) and 0,7 g of monohydrated lithium hydroxyde (0.016 mole) in 35 mL of water are added dropwise over a period of 1h30 to a solution of 12 g of the amine $B_2$ prepared in the first step (0.050 mole) heated under reflux, in 125 mL of ethanol and 25 mL of water. The reflux is maintained for 10 hours after the addition of the reactants. The ethanol is then evaporated under vacuum. The resulting orange oil is washed seven times with 50 mL of dichloromethane. The product is collected by evaporation, protonated with a solution of hydrochloric acid at 5% in ethanol, and then purified by recrystallization in a mixture of ethanol and hydrochloric acid at 5%. The expected product is collected as 1.26 g of a white powder.

$^1$H NMR (D2O) δ 2.59 (s, 2H, NH—$CH_2$—$CH_2$—N—); pH=9 2.72 (t, 2H, NH—$CH_2$—$CH_2$—N—); 3.16 (s, 2H, $CH_2$—$CO_2H$); 3.68 (s, 2H, $C_5H_4$—$CH_2$); 3.70 (s, 2H, $C_5H_4N$—$CH_2$'); 7.35 (t, 1H, $H_5$—Py); 7.39 (t, 1H, $H_5$'—Py); 7.81 (t, 1H, $H_4$—Py); 7.84 (t, 1H, $H_4$'—Py); 8.41 (d, 1H, $H_6$—Py); 8.45 (d, 1H, $H_6$'—Py); 8.53 (d, 1H—$H_2$—Py); 8.56 (d, 1H, $H_2$'—Py);

EXAMPLE 5b

Synthesis of Compound of Formula L18

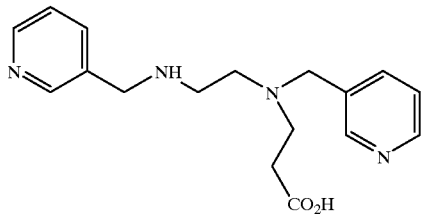

1st step: synthesis if bis-1,6(pyridyl-3) diaza-2,5hexane $B_2$.
2nd step: condensation of the 3-bromopropanoic acid with the amine $B_2$.

A solution of 1.27 g of 3-bromopropanoic acid (0.008 mole) and 0,7 g of monohydrated lithium hydroxyde (0.016 mole) in 35 mL of water are added dropwise over a period of 2 hours to a solution of 12 g of the amine $B_2$ in 125 mL of ethanol and 25 mL of water heated under reflux.

The reflux is maintained for 9 hours after the addition of the reactants. The ethanol is evaporated under vacuum and the resulting orange aqueous solution is washed seven times with 50 mL of dichloromethane. The product is collected by evaporation, protonated with a solution at 5% of hydrochloric acid in ethanol and then purified by recrystallization in a mixture of ethanol and hydrochloric acid diluted at 5%. The expected product is collected as 1.12 g of a white powder.

$^1$H NMR (D2O): δ 2.58 (t, 2H, NH—$CH_2$—$CH_2$—N—); pH=9 2.72 (t, 2H, NH—$CH_2$—$CH_2$—N—); 2.91 (t,2H, $CH_2$—$CH_2$—$CO_2H$); 3.16 (t, 2H, $CH_2$—$CH_2$—$CO_2H$); 3.65 (s, 2H, $C_5H_4N$—$CH_2$); 3.68 (s, 2H, $C_5H_4N$—$CH_2$'); 7.34 (t, 1H, $H_5$—Py); 7.37 (t, 1H, $H_5$'—Py); 7.83 (t, 1H, $H_4$—Py); 7.84 (t, 1H, $H_4$'—Py); 8.39 (d,1H, $H_6$—Py); 8.42(d,1H, $H_6$'—Py); 8.52 (d, 1H—$H_2$—Py); 8.56 (d,1H, $H_2$'—Py);

6) The following examples 6a and 6b have in common the first step which is the preparation of the dinitrile according to the condensation (6) and a second step which is the condensation of the benzyle bromide with the dinitrile according to condensation a), followed by a condensation with an acid halide according to (a) and then a hydrogenation step of the two nitrile functions according to (6).

The two first steps are performed as follows:

1st step: preparation of the dinitrile.

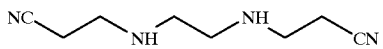

During about one hour, 130 mL of acrylonitrile (1.98 mole) are added to 65 mL of ethylenediamine (0.35 mole).

The bulk medium temperature raises slowly. After stirring at room temperature during four days, a colorless liquid is collected and used without further purification.

$^1$H NMR($D_2O$): δ 2.65(t, 4H, $CH_2$—CN); 2.73(s, 4H, NH—$CH_2$—$CH_{2-NH}$); 2.90(t, 4H, $CH_2$—$CH_2$—CN).

2nd step: preparation of compound S by condensation of the benzyle bromide with the dinitrile.

A solution of 15 g of the dinitrile obtained in the first step (0.090 mole) and 5.75 g of potassium carbonate (0.047 mole) in 150 mL of ethanol is heated under reflux.

A solution of 3 mL of benzyle bromide in 15 mL of ethanol is then added over a period of 1 hour. The resulting solution is then kept under reflux for 3 hours after the reactant addition. The solvent is then evaporated under vacuum and the resulting orange oil is dissolved in 150 mL of water. The benzylnitrile is extracted by the dichloromethane. After drying over magnesium sulfate, filtration and evaporation, 6.2 g of product are collected. This product is then purified by column chromatography, to yield 3.6 g of a pure yellow oil.

$^1$H NMR (D2O): δ 2.43(t,2H, $CH_2$—CN); 2.44 (t,2H, $CH_2$'—CN); 2.67 (s,4H, NH—$CH_2$—$CH_2$—NH); 2.81 (t,2H, $CH_2$—$CH_2$—CN); 2.81 (t,2H, $CH_2$'—$CH_2$—CN); 3.64 (s,2H, $CH_2$—Ph); 7.32 (s,5H, H—Ph)

EXAMPLE 6a

Synthesis of Compound of Formula L19

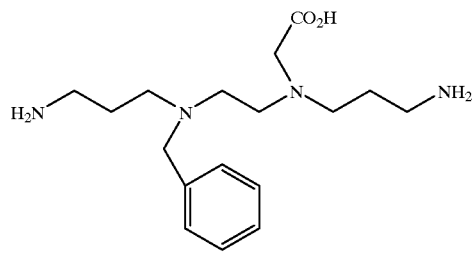

1st step: preparation of the dinitrile.

2nd step: preparation of compound S by condensation of the benzyl bromide with the dinitrile.

3rd step: condensation of the bromoethanoic acid with the benzyldinitrile S.

A solution of 3.1 g of the benzyl dinitrile S obtained in the second step (0.012 mole) in 35 mL ethanol and 7 mL of water are heated to reflux. A solution of 1.65 g of bromoethanoic acid (0.011 mole) and 1 g of monohydrated lithium hydroxyde (0.024 mole) in 35 mL of water is added over a period of about one hour. The reflux is maintained during 9 hours after the end of the reactant addition. The solvent is then removed by evaporation under vacuum and the resulting orange oil is dissolved in 50 mL of water. The expected product is collected by extraction with the dichloromethane and purified by column chromatography.

$^1$H NMR (D2O): δ 2.43 (t,2H, $CH_2$—CN); 2.44 (t,2H, $CH_2$'—CH); 2.67 (s,4H, NH—$CH_2$—$CH_2$—NH); 2.81 (t,2H, $CH_2$—$CH_2$—CN); 2.81 (t,2H, $CH_2$'—$CH_2$—CN); 3.12 (t,2H, $CH_2CO_2H$); 3.64 (s, 2H, $CH_2$—Ph); 7.32 (s,5H, H—Ph)

4th step: Reduction of the nitrile functions by dihydrogene in the presence of Raney Nickel.

A solution of 2 g of the product obtained in the 3rd step in 30 mL of ethanol and 1 g of Raney Nickel are mixed in a reactor. The hydrogenation is then carried out under a pressure of about 50 bars during 24 hours.

The catalyst is then removed by filtration and the solvent is evaporated under vacuum. The resulting orange oil is purified by column chromatography. The expected product is then collected as 1.2 g of a yellow oil.

$^1$H NMR (D2O): δ 1.72 (quint,2H, $CH_2$—$CH_2$—$CH_2$—$NH_2$); pH=9 1.72 (quint, 2H, $CH_2$—$CH_2$'—$CH_2$—$NH_2$); 2.63 (t, 2H, NH—$CH_2$—$CH_2$—$NH_2$); 2.65 (t, 2H, NH—$CH_2$—$CH_2$'—$NH_2$); 2.68 (t, 2H, $CH_2$—$CH_2$—$CH_2$—$NH_2$); 2.69 (t, 2H, $CH_2$'—$CH_2$—$CH_2$—$NH_2$); 2.71 (t, 2H, $CH_2$—$NH_2$); 2.73 (t,2H, $CH_2$'—$NH_2$); 2.84 (t, 2H—$CH_2CO_2H$); 3.64 (s, 2H, $CH_2$—Ph); 7.32 (S, 5H, H—Ph)

EXAMPLE 6b

Synthesis of Compound of Formula L20

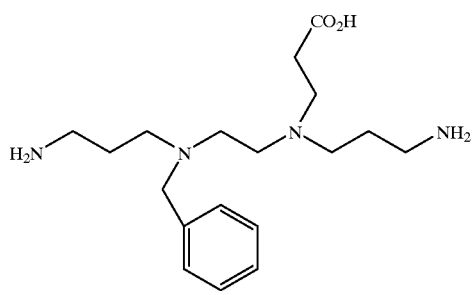

1st step: preparation of the dinitrile.
2nd step: preparation of compound S by condensation of the benzyle bromide with the dinitrile.
3rd step: condensation of the 3-iodopropanoic acid with compound S.

The benzyl dinitrile S obtained in the second step (0.014 mole) is heated under reflux in 42 mL of ethanol and 8.4 mL of water. A solution of 2.8 g of 3-iodopropanoic acid (0.014 mole) and 1.18 g of monohydrated lithium hydroxyde (0.028 mole) in 35 mL of water, is then added slowly over a period of about one hour. The resulting solution is kept under reflux during 9 hours after the end of the reactant addition. The solvent is then evaporated under vacuum and the resulting orange oil is dissolved in 50 mL of water. The expected product is extracted by the dichloromethane and then purified by column chromatography.

$^1$H NMR (D2O): δ 2.41 (t,2H, $CH_2$—CN); 2.42 (t,2H, $CH_2$—CN); 2.68 (s,4H, NH—$CH_2$—$CH_2$—NH); 2.79 (t,2H, $CH_2$—$CH_2$—CN); 2.79 (t,2H, $CH_2$—$CH_2$—CN); 3.12 (t,2H, $CH_2$—$CO_2$H); 3.15 (t,2H,—$CH_2$—$CH_2$—$CO_2$H); 3.66 (s,2H, $CH_2$—Ph); 7.35 (s,5H, H—Ph)

4th step: reduction of the nitrile functions by $H_2$ with Raney Nickel.

A solution of 2 g of the product obtained in the 3rd step, in 30 mL of ethanol and 1 g of Raney Nickel are mixed in a reactor. The hydrogenation reaction is carried out under a pressure of hydrogen of 50 bars during 24 hours. The catalyst is then removed by filtration and the solvent by evaporation under vacuum. The resulting orange oil is purified by liquid column chromatography. The expected product is collected as 1.05 g of yellow oil.

$^1$H NMR (D2O); δ 1.70 (quint,2H, $CH_2$—$CH_2$—$CH_2$—$NH_2$); pH=9 1.70 (quint,2H, $CH_2$—$CH_2$—$CH_2$—$NH_2$); 2.59 (t,2H, NH—$CH_2$—$CH_2$—NH); 2.61 (t,2H, NH—$CH_2$—$CH_2$'—NH); 2.66 (t,2H, $CH_2$—$CH_2$—$CH_2$—$NH_2$); 2.70 (t,2H, $CH_2$—$CH_2$—$CH_2$—$NH_2$); 2.73 (t,2H, $CH_2$—$NH_2$); 2.74 (t,2H, $CH_2$'—$NH_2$); 2.84 (t,2H,—$CH_2$—$CO_2$H); 3.11 (t,2H,—$CH_2$—$CH_2$—$CO_2$H); 3.64 (s,2H, $CH_2$—Ph); 7.33 (s,5H, H—Ph)

EXAMPLE 7

Synthesis of Compounds According to Condensation a) by Reaction of an Alkyl Chloride with an Amine The general conditions used are mainly the following:

A solution of 0.1 mole of amine in 100 mL of toluene is heated under reflux in the presence of 0.1 mole of sodium amide. A solution of 0.1 mole of alkyl chloride in 100 mL of toluene is slowly added. The heating is maintained for one hour. After cooling 100 mL of water is added to the bulk solution. The organic phase is collected, evaporated under vacuum and the resulting product is dissolved in ethanol and precipitated by bubbling hydrogen chloride. The product is collected by filtration, washed with ethanol and recrystallized in a water/hydrochloric acid/ethanol mixture.

Following the above procedure, the compounds listed in Table II can be prepared by reacting an amine HN($R_2$, $R_3$) and a chloride $R_1$—Cl, the meanings of the substituants being as indicated.

TABLE II

| Expected Compound | $R_1$ | $R_2$ | $R_3$ |
|---|---|---|---|

TABLE II-continued

| Expected Compound | R₁ | R₂ | R₃ |
|---|---|---|---|

EXAMPLE 8

Synthesis of Compounds According to Condensation c) by Reaction of a Piperazinone and an Alkyl Chloride The condensation is generally carried out according to the following procedure:

1st step: Synthesis of the piperazinone.

A solution of 0.15 mole of ethyle chloracetate (JANSSEN CHIMICA, ref. 22041.22) in 100 mL of ethanol is slowly added to 1 mole of ethylenediamine in 300 mL of ethanol, followed by 0.15 mole of sodium ethylate. The precipitate is removed by filtration, the filtrate is evaporated and the excess of ethylenediamine is distilled off. The piperazinone is then formed by heating at 200° C. under reduced pressure (5 mmHg) and recrystallized in an acetone/petroleum ether mixture.

2nd step: Condensation of an acid chloride with the piperazinone.

A solution of 0.1 mole of piperazinone in 100 mL of toluene is heated under reflux in the presence of 0.1 mole of sodium amide. The acid chloride (0.1 mole) is then slowly added and the heating is maintained during one hour. After cooling, the bulk medium is washed with water, evaporated to dryness and the resulting product is used without further purification.

3rd step: Hydrolysis of the piperazinone.

The compound obtained in the previous step is heated under reflux during 10 hours in 100 mL of water and 100 mL of concentrated sulfuric acid. After concentrating the solution to 100 mL, the acid is precipitated by adding ethanol and cooling at −15° C. The expected product is collected by filtration, washed with ethanol and recrystallized in a water/sulfuric acid/ethanol mixture.

In tables IIIa and IIIb are listed the product obtained by reaction of chlorides $R_1Z$ and piperazinone.

TABLE IIIa

| monocondensation | | |
|---|---|---|
| Expected Compound | R1 Cl | Piperazinone |

TABLE IIIa-continued monocondensation

| Expected Compound | R1 Cl | Piperazinone |
|---|---|---|
|  |  |  |

TABLE IIIb dicondesation

| Expected Compound | R1 Cl | Piperazinone |
|---|---|---|
| 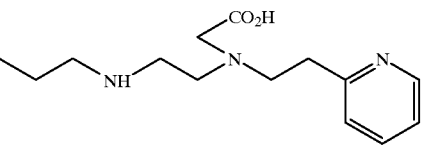 3 | 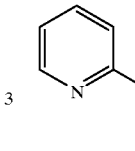 | 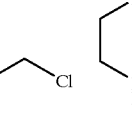 |
| 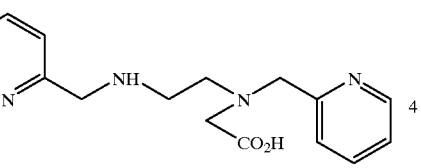 4 | 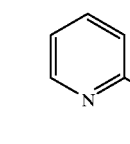 | 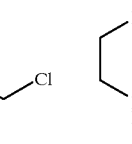 |
| 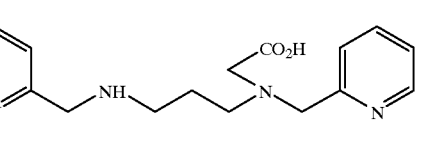 5 | 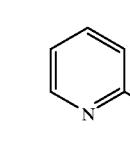 | 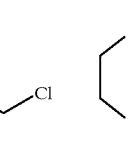 |
| 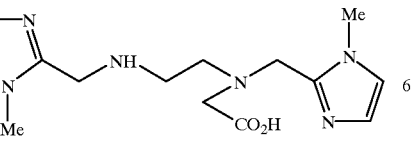 6 | 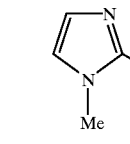 | 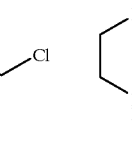 |
| 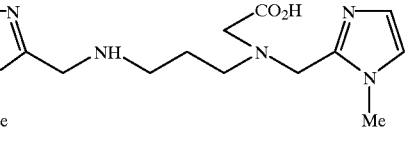 7 | 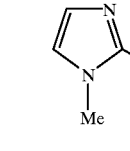 | 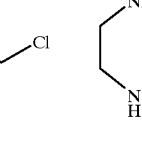 |
| 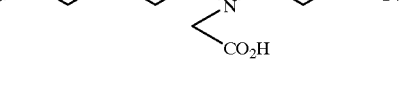 14 |  | 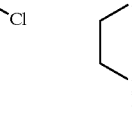 |

EXAMPLE 9

Synthesis of Compounds by Reaction of a Secondary Amine with an Ester Halide

The ethyl bromoacetate (JANSSEN CHIMICA, ref. 15859.48) reacts with a secondary amine $(R_2, R_3)NH$ according to the following procedure: 0.1 mole of an amine is heated under reflux with 0.1 mole of ethyl bromoacetate and 0.1 mole of sodium carbonate in 200 mL of ethanol, during several hours (4 to 12). 100 mL of ethanol is then removed by distillation and crushed ice is added to the resulting solution. The precipitate is collected by filtration and then dried.

The isolated solid, without further purification, is heated under reflux during 2 hours in 50 mL of water and 50 mL of concentrated sulfuric acid (d=1.83). The acid is then precipitated by adding ethanol and cooling at −15° C. during 24 hours. The precipitate is then filtered and recrystallized in a water/sulfuric acid/ethanol mixture. After filtration, the acid is washed with ethanol, dried and collected as a white powder.

In Table IV are listed the products obtained starting from different amines.

TABLE IV

| Expected Compound | Secondary Amine | Treatment |
|---|---|---|
| (structure 3) | (structure) | hydrolysis |
| (structure 4) | (structure) | hydrolysis |
| (structure 5) | (structure) | hydrolysis |
| (structure 6) | (structure) | hydrolysis |
| (structure 7) | (structure) | hydrolysis |
| (structure 14) | (structure) | hydrolysis |

EXAMPLE 10

Synthesis According to Condensation d) of a Cyclic Compound of Formula

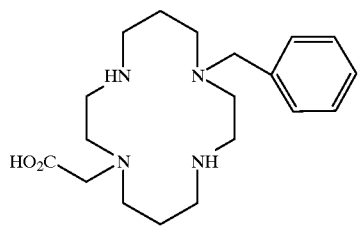

This synthesis is realised according to the following reactions:

1: reaction of a dinitrile with a benzyl bromide.

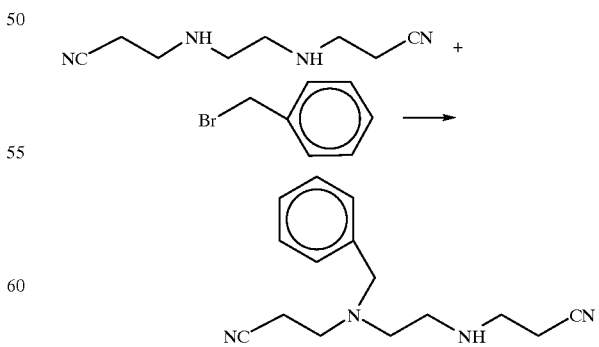

2: reduction of the nitrile functions to yield the diamino compound of formula:

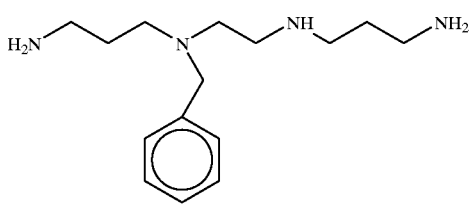

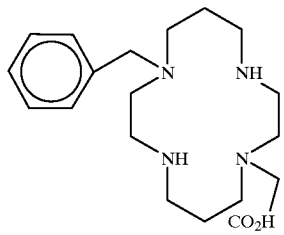

3: condensation with a dialdehyde in the presence of hexahydrated nickel chloride according to:

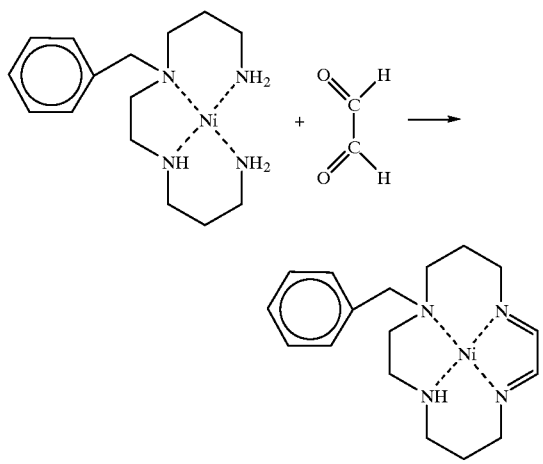

4: Hydrogenation followed by a reaction with NaCN

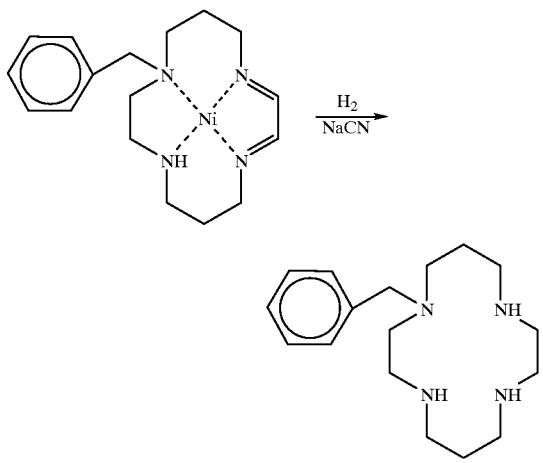

5: Binding of a chain containing a carboxylate function.

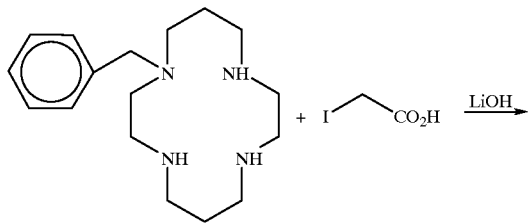

These reactions are carried out in the following manner:
1: reaction of a dinitrile with a benzylbromide.

After mixing rapidly 35 g of N,N'-bis (cyano-2-ethyl)-diamino-1,2 ethane in 274 mL of ethanol, 24.8 mL of benzyl bromide (0.210 mole) is slowly added. This solution is heated under reflux during 2 hours. After cooling, at room temperature the white precipitate is removed by filtration, the filtrate is evaporated and 76.5 g of a yellow oil is collected.

To this oil are added 111 mL of distilled water and 58 mL of chloroform. After stirring, the pH is raised to 8 by adding 11 mL of a sodium hydroxyde solution at 30%. The organic phase is then isolated, dried over magnesium sulfate, filtered and evaporated to yield 48 g of a yellow oil.

This oil is purified by chromatography on a silica column under moderate pressure and 8.6 g of an oil is collected which corresponds to the monobenzyl product.

2: reduction.

The hydrogenation is performed on 7 g of the oil dissolved in 35 mL of ethanol. The catalyst is then removed by filtration on Celite and the filtrate is evaporated to dryness.

Then, 3 mL of concentrated hydrochloric acid and 30 mL of ethanol are added. The expected product is isolated as a hydrochlorate.

3: condensation with the dialdehyde.

To 4 g of N-Benzyl bis (amino-3-propyl) diamino-1,2-ethane dissolved in 60.6 mL of water, are added 3.6 g of hexahydrated nickel chloride. The bulk is kept at 5° C. and 2.5 mL of glyoxal at 40% in aqueous solution is then slowly added.

4: Hydrogenation and decomplexation.

After one night at room temperature the hydrogenation is performed under a pressure of 20 bars in a vessel adapted for such high pressure, in the presence of 1.5 g of Raney Nickel catalyst at 50% in water.

After reaction, the catalyst is removed by filtration, 3.8 g of sodium cyanide are added to the filtrate which is then heated under reflux for 2 hours.

After cooling, the product is extracted several times from the solution by chloroform. This organic phase is dried over magnesium sulfate and then evaporated to collect the expected product.

5: Addition of the carboxylate function.

To 3 g of N-Benzyl cyclam (0.01 mole), dissolved in 45 mL of ethanol and 9 mL of water, are added 0.168 g of monohydrated lithium hydroxyde (0.004 mole). The solution is then maintained at 3° C. and 0.002 mole of bromoacetic acid in 7 mL water are slowly added. The solution is heated under reflux during 21 hours and the solvents are then evaporated. The resulting solid is dissolved in 10 mL of water and 15 mL of chloroform. After several extractions with chloroform, the aqueous phase is isolated and concentrated. After the slow addition of 3 mL of concentrated hydrochloric acid, the disubstituted cyclam is precipitated by adding 30 mL of ethanol and cooling the solution at −15° C. during one day. The precipitate is filtered and recrystallized in an ethanol/water/HCl mixture.

EXAMPLE 11

General Preparation Precedure of Complexes II of Formula X=LCo$^{II}$

Under argon atmosphere, 0.2 10$^{-3}$ mole of ligand L is dissolved in 20 mL of degassed and deionized water.

The pH of the solution after complete dissolution of L is different from the pH of pure water and depends on the nature of L and on the mode of preparation (as an example the pH will differ if the compound is obtained by distillation or as a salt resulting from an acid precipitation).

The pH of the solution is then adjusted, by adding an acid or a base, to the value at which the neutral form LH and the anionic form L$^-$ of ligand L are dominant. The introduction of the cobalt salt, when performed under argon, leads to the formation of the complex LCo$^{II}$. The presence of LCo$^{II}$ is checked and followed by UV-Visible spectrophotometry since a charge transfer band L→Co$^{II}$ exists between 190 and 290 nm, depending on the ligand. As an illustration, in Table V are listed the wavelength values of the charge transfer bands characteristic of the LCo$^{II}$ complex for several ligands L, as well as the pH values at which the intensities of these bands are maximum.

TABLE V

| Ligand | λ max (nm) | pH |
|---|---|---|
| L1 | 197 | 6.9 |
| L2 | 206 | 8.7 |
| L6 | 204 | 6.8 |
| L9 | 255 | 5.5 |
| L10 | 255 | 5.1 |
| L12 | 212 | 5.1 |
| L14 | 266 | 5.0 |
| L16 | 250 | 8.0 |

It is important to note that since the Co$^{2+}$ ion usually requires an octahedral coordination in solution, one or two supplementary coordinations should occur since the ligands of this invention are tetradentate or pentadentate and cannot complete the coordination scheme of one cobalt ion. These coordinants may be counter ions as chloride or acetate, hydroxyde ions, OH$^-$, in rather basic media, or also water molecules.

The formation of complexes LCo$^{II}$ can also be followed by 1H NMR spectroscopy. After metal complexation, the signals of the protons of ligand L appear in a frequency range of 250 to −100 ppm which differs from the 0 to 10 ppm range of the ligand itself. Such a large change in the frequency range of the LCo$^{II}$ proton resonance signals is a result of the metal charge density distribution on the carbon atom of the ligand L since the external electronic configuration of the cation Co$^{2+}$ is 3d$^7$.

EXAMPLE 12

Preparation of the Metal Complex of Formula Co$^{II}$ (C$_6$H$_5$CH$_2$—NH—(CH$_2$)$_2$—NH—(CH$_2$)$_2$—NH—(CH$_2$)$_2$COOH In 20 mL of water are dissolved 96 mg of [C$_6$H$_5$CH$_2$—NH—(CH$_2$)$_2$—NH—(CH$_2$)$_2$—NH—(CH$_2$)$_2$—COOH, 2H$_2$SO$_4$, H$_2$O)], at a pH of 7.47, under argon at 22° C. After complete dissolution of the ligand (compound of this invention), the pH of the solution is 2.25.

By adding 50 mg of tetrahydrated cobalt acetate to the solution, the pH is increased and is stable at the value of 3.51.

The pH is then raised to the expected value by adding NaOH to the solution.

In order to have the metal complex at the concentration of 7.10$^{-3}$M, the pH must be of 7.37.

Each step of this preparation is effected under inert atmosphere and the reactants are previously conditionned so that no trace of oxygen is introduced in the set-up.

If these different steps are performed in the presence of dioxygen, the metal complex will react with O$_2$ and yield the peroxo dimer LCoO$_2$CoL where L represents the polynitrogenated compound of the invention.

EXAMPLE 13

Determination of the Amount of O$_2$ Absorbed by a Complex of this Invention The complex LCo$^{II}$ when exposed to dioxygen leads quickly to a μ-peroxo complex LCoO$_2$CoL according to:

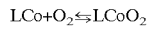

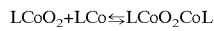

The amount of dioxygen absorbed and the kinetics of this absorption depend on several parameters such as the pH. This is illustrated on FIG. 1 for the ligand L7. The absorption evaluations are made by volumetry, potentiometry or UV-Visible spectrophotometry.

EXAMPLE 14

Determination of the Amount of Dioxygen Absorbed by a Complex of the Invention A-Volumetric determination.

General method.

A direct measurement of the amount of O$_2$ absorbed by a metal complex solution is effected in the following manner:

In a three necked round bottom flask of 100 mL capacity, 20 mL of an aqueous solution of ligand at the concentration of 10$^{-2}$M and at a given pH is in equilibrium with a gas mixture containing dioxygen at a known partial pressure. The temperature of the whole set-up is kept constant at 25° C.

A calibrated capillary tube, containing a mercury index, is connected to the flask as well as a pressure transducer and a bent glass tube that contains the metal salt.

When all these different parts of the set-up are in equilibrium with each other and strictly isolated from outside, the metal salt is introduced in the stirred solution by rotating the bent tube. The decrease of pressure inside the set-up, induced by the immediate absorption of O$_2$ is compensated by a volume change as indicated by the mercury index move.

Once the index stops moving, the solution has reached a new equilibrium and the measure of O$_2$ absorbed volume is directly readable on the capillary tube. It is then possible to evaluate the XO$_2$X and X concentrations ans thus the KO$_2$ value. However the O$_2$ concentration at equilibrium must be computed for each measurement, the partial pressure of O$_2$ in the gas mixture being reduced after absorption.

Measurement performed with the pF (C$_6$H$_4$)—CH$_2$—NH—(CH$_2$)$_2$NH—(CH$_2$)$_2$—NH—(CH$_2$)$_2$—COOH ligand (pF=parafluoro).

To 20 mL of an aqueous solution of the above ligand at a concentration of 10$^{-2}$M, at a pH of 7.56, is added 0.053 g of cobalt acetate. The volume of O$_2$ absorbed is 0.294 mL. This volume corresponds to 1.19.10$^{-5}$ mole of O$_2$ under the temperature and pressure conditions of the experiment.

According to the protonation and metallation constants of the ligand, it is then possible to evaluate a KO$_2$ value of 2.6×10$^4$.

This value is confirmed by an other experiment realised with a solution, of this same ligand, at the same initial concentration, at an initial pH of 8.10 before introduction of cobalt acetate. The volume measured in the capillary tube is 0.464 mL and corresponds to an amount of $O_2$ absorbed of $1.86.10^{-5}$ mole.

B-Potentiometric titration.

By titrating a solution containing a ligand and a metal salt in equilibrium with a gas mixture containing dioxygen, the $KO_2$ value can be computed by difference with the titration performed under nitrogen.

C-UV.Visible Spectrophotometry.

An aqueous solution containing a ligand and a metal salt, at any relative concentration, does not show any absorption peak between 300 and 500 nm if it is kept under a non oxygenated atmosphere.

If this solution is contacted with a gas mixture containing dioxygen, a large absorption peak appears in the range 300 to 500 nm and more generally, between 300 and 400 nm. The intensity of the absorption peak varies as a function of the solution pH and of the $O_2$ partial pressure in the gas mixture in equilibrium with the solution.

On Table VI are summarized the wavelengths of the peaks, characteristic of the $LCoO_2CoL$ complexes (of the charge transfer from Cobalt to dioxygen), as well as the pH values of the studied solutions.

TABLE VI

| Ligand | λ max (nm) | pH |
|---|---|---|
| L1 | 314 | 4.6 |
| L2 | 370 | 7.0 |
| L3 | 368 | 5.9 |
| L4 | 368 | 6.2 |
| L6 | 375 | 6.0 |
| L7 | 371 | 5.8 |
| L8 | 328 | 6.3 |
| L9 | 370 | 5.7 |
| L10 | 365 | 7.7 |
| L12 | 315 | 5.5 |
| L13 | 358* | 6.5 |
| L14 | 320* | 6.7 |
| L16 | 374 | 6.0 | shoulder ; ill defined λ

The UV-Visible spectra recorded for ligands of this invention in the presence of cobalt acetate and in equilibrium with air, at two different pH, indicate that the ratio of the peak intensities (at their maximum) corresponds exactly to the ratio of the volumes of $O_2$ absorbed as measured by volumetry in the same pH and temperature conditions.

Stability of the $LCoO_2CoL$ complexes:

The dioxygenated complexes $LCoO_2CoL$ are often unstable and form species that do not react with dioxygen. These species result:

either from a metal centered oxidation of the μ-peroxo complex which leads to a $LCo^{III}$ species.

either from an oxidation of the organic ligand that change the structure and thus the properties of the resulting complex, or from a ligand exchange (other than L) from the cobalt coordination sphere leading to a new stable, coordinatively saturated species.

The loss of the $O_2$ absorption capacity of $LCo^{II}$ (or degradation) is followed as a function of time by measuring the intensity of the UV-Visible peak due to the charge transfer colbalt→dioxygen, of the μ-peroxo $LCoO_2CoL$ complexes.

The mechanism and the kinetics of the degradation depend on the structure of ligand L. A complete degradation is observed for the linear pentadentate ligands after only a few hours while several months are necessary for the linear tetradentates or the branched pentadentates.

The NMR study of the degraded solutions containing linear pentadentate ligands indicates that an oxidation of the metal center occured which lead to the formation of $LCo^{III}$. Such solutions are however quite appropriate for the separation of the dioxygen from a gas mixture containing dioxygen, if the desorption is effected by electrochemical means. The $Co^{III}$ complexes are, in such a case, reduced into $Co^{II}$ complexes in the cathode compartment of the electrochemical cell and get then back their capacity to bind dioxygen.

These observations are illustrated on FIGS. 2 and 3 for two selected series of ligands. As examples, the linear pentadentate ligand L8 is totally degraded in 2.5 hours while the tetradentate ligand L2 has lost 75% of its original capacity in 85 days and the branched pentadentate ligand L16 has lost 70% of its initial capacity in 110 days.

EXAMPLE 15

Desorption of Bound $O_2$

The desorption of the bound dioxygen may be effected by decreasing the $O_2$ partial pressure if the affinity constant is lower than $10^7 M^{-1}L$, or by electrochemical oxidation.

These two methods are tested for the compounds of this invention.

1. Difference in partial pressure.

The amount of $O_2$ desorbed by decreasing the $O_2$ partial pressure is evaluated mainly by UV.Visible spectrophotometry.

The intensity of the absorption peak between 300 and 400 nm is directly proportionnal to the concentration of $XO_2X$.

The difference of the peak intensities as recorded for solutions in equilibrium with an atmosphere rich in dioxygen and with an $O_2$ depleted atmosphere, is a direct measure of the amount of $O_2$ desorbed.

Such measurements are illustrated on FIG. 4.

2. Desorption by electrochemical oxidation.

The electrochemical oxidation of $XO_2X$ induces the desorption of $O_2$ according to the following reaction:

$$XO_2X \rightarrow 2X^+ + O_2 + 2e^-$$

The value of the potential to be applied for the oxidation to occur and the dioxygen to be unloaded, is determined by using an electrochemical cell of 20 mL volume capacity.

This electrochemical cell possess two compartments separated by anionic membrane (RAI4035). The appropriate electrodes are used which have been rated as the best for the electron transfer kinetics. The current going through the cell is recorded for each potential applied between the two electrodes. The current intensity-potential curves indicate the potential value required for the oxidation and reduction reactions to occur. The amount of $O_2$ desorbed is measured by connecting a volumeter (Emerson-Brooks) to the anodic compartment of the cell. The volume of $O_2$ desorbed is then recorded as a function of time.

We claim:

1. A process for recovering oxygen from a gas mixture that contains $O_2$, which comprises:

(a)—contacting a gas mixture with a metal complex consisting of a metal atom and a polynitrogenated ligand having five coordinating functions and the formula:

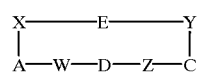

in which
X and Z, identical or different, are selected from

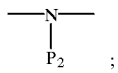
;

wherein $P_2$ is selected from hydrogen, $C_1$–$C_4$ alkyl and $C_1$–$C_4$ alkyl substituted by one or several groups selected from
—COR in which R is selected from hydroxyl;
$NH_2$;
—$NH(C_1$–$C_4$ alkyl); —$N(C_1$–$C_4$ alkyl)$_2$;
—O—($C_1$–$C_4$ alkyl),
phenoxy
phenoxy substituted by one to three groups selected from halogen, $C_1$–$C_4$ alkyl, $C_1$–$C_4$ alkoxy, and nitro;
phenyl;
phenyl substituted by one to three substituents selected from halogen, $C_1$–$C_4$ alkyl, $C_1$–$C_4$ alkoxy and nitro;
$C_1$–$C_4$ alkyl;
$C_1$–$C_4$ alkoxy;
halogen and
nitro; and
an aromatic heterocycle selected from pyridine, imidazole, quinoline, isoquinoline, pyrrole, pyrimidine, pyrazine, pyridazine, indole, carbazole, purine, phenazine, thiazole, isothiazole, oxazole, isoxazole, said aromatic heterocycle substituted with at least one radical selected from $C_1$–$C_4$ alkyl and $C_1$–$C_4$ alkyl substituted by at least one group selected from
phenyl;
phenyl substituted by one to three substituents selected from halogen, $C_1$–$C_4$ alkyl, $C_1$–$C_4$ alkoxy and nitro;
$C_1$–$C_4$ alkyl;
$C_1$–$C_4$ alkoxy;
halogen and
nitro;
Y and W, identical or different, represent

in which
$P_2$ is a defined above, it being understood that one of W, X, Y, and Z is

in which $P_2$ is $C_1$–$C_4$ alkyl substituted by —COR;
A, E, C and D, identical or different, are selected from $C_1$–$C_3$ alkylene and $C_1$–$C_3$ alkylene substituted with at least one radical selected from $C_1$–$C_4$ alkyl and $C_1$–$C_4$ alkyl substituted at least one group selected from:
phenyl;
phenyl substituted by one to three substituents selected from halogen, $C_1$–$C_4$ alkyl, $C_1$–$C_4$ alkoxy and nitro;
$C_1$–$C_4$ alkyl;
$C_1$–$C_4$ alkoxy;
halogen and
nitro;
with the proviso that among the five coordinating functions only one is a —COR group, the other being either

or an aromatic heterocycle;
a metal complex prepared starting with a ligand of formula:

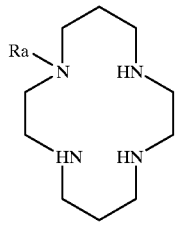

in which Ra represents —$(CH_2)_n$—COOH with n varying from 1 to 3, is excluded;
in conditions which favor the absorption of $O_2$ from the gas mixture by the metal complex to yield the dimer $C_pO_2C_p$ where $C_p$ is a metal complex molecule,
(b)—desorbing the bound oxygen,
(c)—recovering the desorbed oxygen, the metal complex being immobilized on a $O_2$, permeable membrane, said membrane being made of a polymer film which has one side in contact with a gas mixture containing oxygen, while desorption of bound $O_2$ occurs at the other side.

2. The process according to claim 1 wherein the metal atom of the complex is selected from the group consisting of Co, Ni, Fe and Mn.

3. The process according to claim 1 wherein the aromatic heterocycle is selected from the group consisting of pyrimidyl and imidazolyl.

4. The process according to claim 1 wherein the oxygen is desorbed by applying a temperature gradient between the two sides of said oxygen permeable membrane when the metal complex is in a solution and immobilized on said oxygen permeable membrane.

5. The process according to claim 1 wherein the ligand is of the formula:

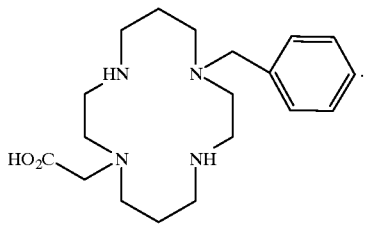

6. The process according to claim 1 wherein the metal complex is in an aqueous or partially aqueous solution at a concentration of 0.1 M to 1 M at a pH of 6 to 8.

7. The process according to claim 1 wherein desorption is effected by electrochemical oxidation.

8. The process according to claim 1 wherein desorption is effected by vacuum.

9. The process according to claim 9 wherein the partial pressure of $O_2$ in the atmosphere contacted with the metal complex in solution is reduced.

10. The process according to claim 1 wherein the metal complex is in a solution immobilized on a membrane and desorption is effected by applying a temperature gradient between two sides of the membrane.

* * * * *